United States Patent
Masuda et al.

(10) Patent No.: US 12,263,180 B2
(45) Date of Patent: Apr. 1, 2025

(54) METHOD FOR TREATMENT OF COVID-19-ASSOCIATED CONDITIONS

(71) Applicant: Rigel Pharmaceuticals, Inc., South San Francisco, CA (US)

(72) Inventors: Esteban Masuda, Menlo Park, CA (US); Vadim Markovtsov, San Mateo, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 989 days.

(21) Appl. No.: 17/323,901

(22) Filed: May 18, 2021

(65) Prior Publication Data

US 2021/0283152 A1    Sep. 16, 2021

Related U.S. Application Data

(63) Continuation of application No. PCT/US2021/021951, filed on Mar. 11, 2021.

(60) Provisional application No. 62/988,876, filed on Mar. 12, 2020, provisional application No. 63/038,570, filed on Jun. 12, 2020.

(51) Int. Cl.
| | |
|---|---|
| A61K 31/5383 | (2006.01) |
| A61K 31/155 | (2006.01) |
| A61K 31/245 | (2006.01) |
| A61K 31/427 | (2006.01) |
| A61K 31/4706 | (2006.01) |
| A61K 31/4748 | (2006.01) |
| A61K 31/519 | (2006.01) |
| A61K 31/573 | (2006.01) |
| A61K 31/675 | (2006.01) |
| A61K 31/7048 | (2006.01) |
| A61K 39/42 | (2006.01) |
| A61P 31/14 | (2006.01) |
| C07K 16/10 | (2006.01) |

(52) U.S. Cl.
CPC .......... *A61K 31/675* (2013.01); *A61K 31/155* (2013.01); *A61K 31/245* (2013.01); *A61K 31/427* (2013.01); *A61K 31/4706* (2013.01); *A61K 31/4748* (2013.01); *A61K 31/519* (2013.01); *A61K 31/573* (2013.01); *A61K 31/7048* (2013.01); *A61K 39/42* (2013.01); *A61P 31/14* (2018.01); *C07K 16/1003* (2023.08)

(58) Field of Classification Search
CPC ....... A61K 31/5383; A61P 31/12; A61P 11/00
USPC ................................................... 514/230.5
See application file for complete search history.

(56) References Cited

U.S. PATENT DOCUMENTS

| | | |
|---|---|---|
| 8,372,415 B2 | 2/2013 | Sun et al. |
| 2007/0060603 A1 | 3/2007 | Singh et al. |
| 2011/0144059 A1 | 6/2011 | Bhamidipati et al. |
| 2016/0060260 A1 | 3/2016 | Palmer et al. |

FOREIGN PATENT DOCUMENTS

| | | |
|---|---|---|
| WO | WO2003063794 A2 | 8/2003 |
| WO | WO2003063794 A3 | 8/2015 |
| WO | WO2015116729 A2 | 8/2015 |

OTHER PUBLICATIONS

Altomare et al., "Potential Anti-Thrombotic Effect without Accompanying Hemorrhage with Fostamatinib Use in Patients with Immune Thrombocytopenia", Blood, 2019; 134 (Supplement_ 1): 4889.
Astrazeneca, "A Study of Fostamatinib in Subjects With Impaired Kidney Function", https://clinicaltrials.gov/ct2/show/NCT01245790, 2011.
Price et al., "Thrombosis and COVID-19 pneumonia: the clot thickens!", European Respiratory Journal, Jul. 30, 2020; 56(1): 2001608.
Rudnick et al., "Acute Kidney Injury in COVID-19: Another Challenge for Nephrology", American Journal of Nephrology, Oct. 15, 2020; 51(10): 761-763.
Anonymous DOD Supports Phase III Clinical Trial Using Fostamatinib (Tavalisse) Against Covid-19, JPEO-CBRND, Jan. 29, 2021.
Martin et al., Pharmacokinetic Properties of Fostamatinib in Patients With Renal or Hepatic Impairment: Results From 2 Phase I Clinical Studies, Clinical Therapeutics, 37(12):2823-2836, Dec. 2015.
Nadeem et al., Inhibition of spleen tyrosine kinase signaling protects against acute lung injury through blockade of NADPH oxidase and IL-17A in neutrophils and γδ T cells respectively in mice, Int. Immunopharmacol, 68:39-47, Mar. 1, 2019.
Saha et al., Is Fostamatinib a possible drug for covid-19 ?—A computational study, pp. 1-28, May 1, 2020.
Sanderson et al., Syk: A Novel Target for Treatment of Inflammation in Lung Disease, Inflammation & Allergy—Drug Targets, 8(2):87-95, 2009.

(Continued)

*Primary Examiner* — Charanjit Aulakh
(74) *Attorney, Agent, or Firm* — Jones Day

(57) ABSTRACT

Provided herein are a variety of methods that involve administering fostamatinib, an active component thereof or a pharmaceutically acceptable salt thereof to a patient. In some embodiments, the method may comprise administering fostamatinib, an active component thereof or a pharmaceutically acceptable salt thereof to a patient having or suspected of having a COVID-19 infection. In some embodiments, the method may comprise administering fostamatinib, an active component thereof or a pharmaceutically acceptable salt thereof to a patient having, suspected of having or expected to develop acute respiratory distress syndrome, acute kidney injury, and/or thrombosis. In some embodiments, the method may comprise administering fostamatinib, an active component thereof or a pharmaceutically acceptable salt thereof to a patient having, suspected of having or expected to develop symptoms associated with a cytokine response. Aspects of the methods may further include identifying a patient with kidney malfunction, e.g., acute kidney injury, and/or thrombosis.

39 Claims, 3 Drawing Sheets

(56) References Cited

OTHER PUBLICATIONS

Strich et al., Fostamatinib Inhibits Neutrophils Extracellular Traps Induced by COVID-19 Patient Plasma: A Potential Therapeutic, Journal of Infectious Diseases, 223(6):981-984, Dec. 24, 2020.

Van Eeuwijk et al., The Novel Oral Syk Inhibitor, BI1002494, Protects Mice From Arterial Thrombosis and Thromboinflammatory Brain Infarction, Arterioscler Thromb Vasc Biol., 36(6):1247-1253, Jun. 1, 2016.

Zhao et al., Activation of C-Type Lectin Receptor and (RIG)-I-Like Receptors Contributes to Proinflammatory Response in Middle East Respiratory Syndrome Coronavirus-Infected Macrophages, Journal of Infectious Diseases, 221(4):647-659, Feb. 3, 2020.

Al-Harbi et al., "Amelioration of sepsis-induced acute kidney injury through inhibition of inflammatory cytokines and oxidative stress in dendritic cells and neutrophils respectively in mice: Role of spleen tyrosine kinase signaling", Biochimie, 2019, 158: 102-110.

Kost-Alimova et al., "A High-Content Screen for Mucin-1-Reducing Compounds Identifies Fostamatinib as a Candidate for Rapid Repurposing for Acute Lung Injury", Cell Reports Medicine, 2020, 1:100137.

Weinblatt et al., "Treatment of Rheumatoid Arthritis With a Syk Kinase Inhibitor: A Twelve-Week, Randomized, Placebo-Controlled Trial", Arthritis & Rheumatism, 2008, 58(11): 3309-3318.

METHOD FOR TREATMENT OF COVID-19-ASSOCIATED CONDITIONS

CROSS-REFERENCING

This application is a continuation of International Application No. PCT/US2021/021951, filed on Mar. 11, 2021, which claims the benefit of U.S. provisional application Ser. Nos. 62/988,876, filed on Mar. 12, 2020, and 63/038,570, filed on Jun. 12, 2020, which applications are incorporated by reference in their entirety.

INTRODUCTION

Initial reports suggest that COVID-19 is associated with severe disease that requires intensive care in approximately 5% of cases. The most documented reason for requiring intensive care has been respiratory support. Approximately two thirds of patients requiring intensive care have acute respiratory distress syndrome (ARDS) and a relatively high proportion of patients that have ARDS (e.g., between 35 and 50% of the patients) die. ARDS appears to be the most common cause of death among patients that have been infected by COVID-19 (see, e.g., Wang et al JAMA. 2020: 1585). Evidence is also emerging that acute kidney injury can be a severe complication of COVID-19 infection. Acute kidney injury has been reported in up to 25% of critically-ill patients (Gabarre et al. Intensive Care Med. 2020, 46(7): 1339-1348). In addition, it is reported that COVID-19 patients are at increased risk of thrombosis (Khan et al. J. Vasc. Surg. 2020, S0741-5214(20)31157-5).

High levels of inflammatory cytokines have been reported during COVID-19 infection. These cytokines include interferons, interleukins, chemokines, colony-stimulating factors, and tumor necrosis factors and contribute to the symptoms of coronavirus infection. Overproduction of pro-inflammatory cytokines can result in a "cytokine storm," during which inflammation spreads throughout the body via the circulation. One consequence of a cytokine storm is acute lung injury, which can progress to a more severe form called acute respiratory distress syndrome. Another consequence of a cytokine storm includes failure of multiple organs including, e.g., heart failure and acute kidney injury.

SUMMARY

This disclosure provides, among other things, a method for treating acute respiratory distress syndrome, particularly a way to increase the rate of survival of patients. Also provided is a method for treating acute kidney injury, particularly a way to increase the rate of survival of patients. Also provided is a method of treating thrombosis, particularly a way to increase the rate of survival of patients.

Provided herein are a variety of methods that involve administering fostamatinib, an active component thereof or a pharmaceutically acceptable salt thereof to a patient. Also provided are methods for identifying a patient with kidney malfunction, e.g., acute kidney injury, and/or thrombosis (e.g., detecting kidney malfunction and/or thrombosis in a patient) and administering fostamatinib, a pro-drug thereof or a pharmaceutically acceptable salt thereof to the patient.

In some embodiments, the method may comprise administering fostamatinib, an active component thereof or a pharmaceutically acceptable salt thereof to a patient having or suspected of having a coronavirus infection, e.g., a COVID-19, severe acute respiratory syndrome-associated coronavirus (SARS-CoV) or middle east respiratory syndrome-associated coronavirus (MERS-CoV) infection.

In some embodiments, the method may comprise administering fostamatinib, an active component thereof or a pharmaceutically acceptable salt thereof to a patient having, suspected of having or expected to develop acute respiratory distress syndrome.

In some embodiments, the method may comprise administering fostamatinib, an active component thereof or a pharmaceutically acceptable salt thereof to a patient having, suspected of having or expected to develop acute kidney injury.

In some embodiments, the method may comprise administering fostamatinib, an active component thereof or a pharmaceutically acceptable salt thereof to a patient having, suspected of having or expected to develop thrombosis.

In some embodiments, the method may comprise administering fostamatinib, an active component thereof or a pharmaceutically acceptable salt thereof to a patient having, suspected of having or expected to develop symptoms associated with a cytokine response, e.g., a cytokine storm, where a cytokine storm is caused by the overproduction of inflammatory cytokines, e.g., in the lungs and/or kidneys.

In any embodiment, the method may comprise administering fostamatinib, an active component thereof or a pharmaceutically acceptable salt thereof to a patient having, suspected of having or expected to develop acute or multiple organ failure, where the organ failure is believed to be COVID-19 related.

DETAILED DESCRIPTION

Figure 1:
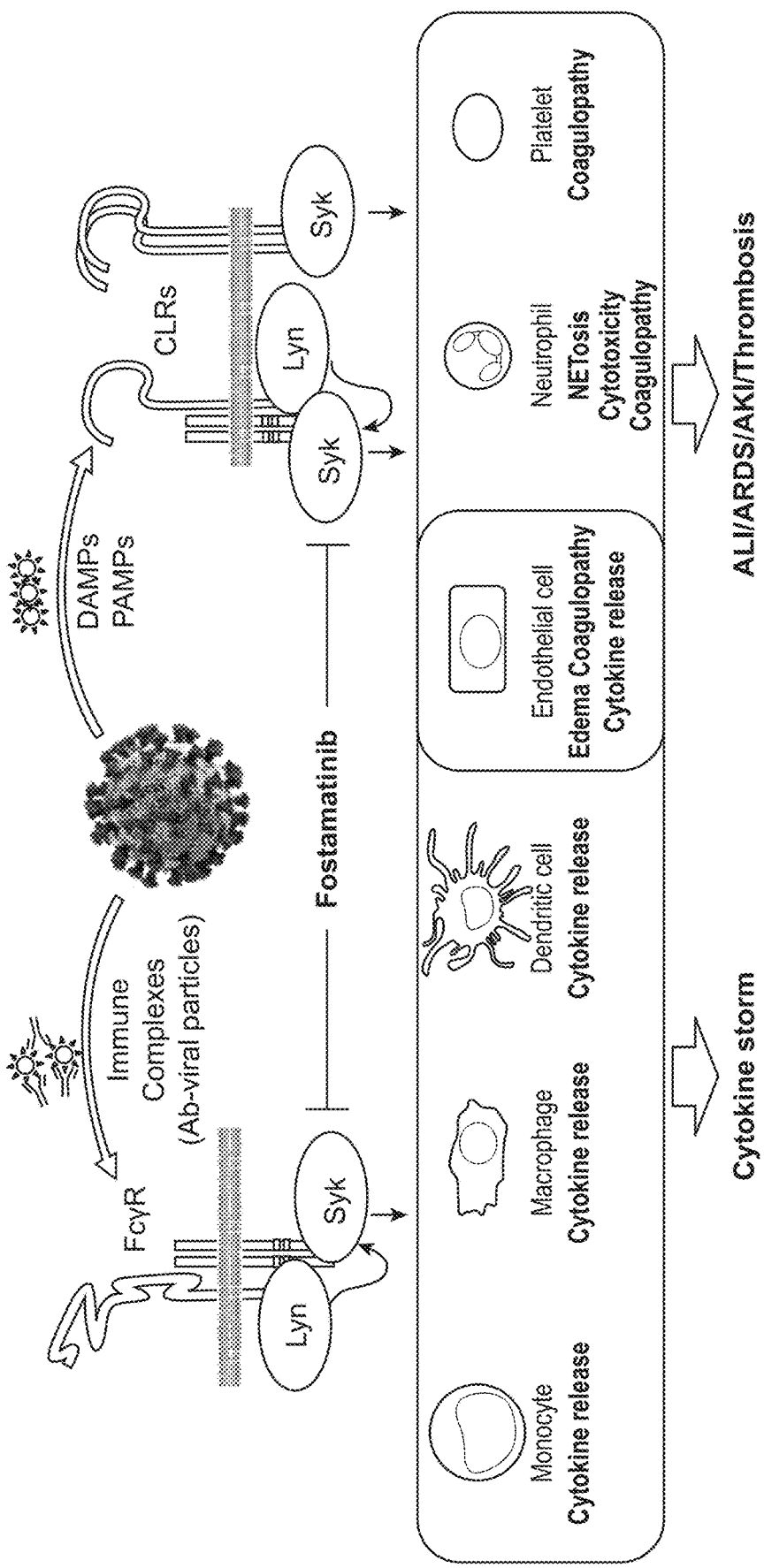
FIG. 1 shows embodiments of targets of fostamatinib.

This disclosure provides, among other things, a method for treating COVID-19 related conditions, e.g., COVID-19-associated ARDS, AKI, or thrombosis, particularly a way to increase the rate of survival of patients that have COVID-19 related conditions, e.g., COVID-19-associated ARDS, AKI, or thrombosis. The present method can also be used to treat other coronaviral-associated diseases such as SARS and MERS because some of the syptoms of all of these coronaviral infections have the same underlying cause (e.g., a cytokine storm in the lungs and/or kidneys).

Provided herein are a variety of methods that involve administering fostamatinib, an active component thereof or a pharmaceutically acceptable salt thereof to a patient.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, CA.).

Terms

The following terms have the following meanings unless otherwise indicated. Any undefined terms have their art recognized meanings.

The term "acute respiratory distress syndrome" or "ARDS" refers to a syndrome characterized by a severe shortness of breath, labored and unusually rapid breathing, low blood pressure, confusion and extreme tiredness. This syndrome can be diagnosed based on a PaO2/FiO2 ratio of less than 300 mmHg despite a PEEP of more than 5 cm H2O (Fan et al JAMA. 319:698-71).

ARDS occurs when fluid builds up in lung alveoli. The fluid prevents the lungs from filling with enough air, limiting the amount of oxygen that reaches the bloodstream which, in turn, deprives the organs of the oxygen they need to function. The symptoms of ARDS can vary in intensity, depending on its cause and severity. Severe shortness of breath—the hallmark of ARDS—usually develops within a few hours to a few days after the COVID-19 infection. Many people who develop ARDS do not survive, and the risk of death increases with age and severity of illness. Of the patients that survive ARDS, some completely recover while others have lasting damage to their lungs. ARDS may be referred to as Acute Lung Injury (ALI) in some publications.

The term "acute kidney injury" or "AKI" or "acute renal injury" or "ARI" or "acute renal failure" or "ARF" as used herein in its conventional sense refers to a syndrome characterized by an abrupt reduction of renal function including, e.g., the ability to excrete waste from a patient's blood. AKI is characterized by a decline of glomerular filtration rate, urine output, or both. This loss of filtration capacity results in retention of nitrogenous (urea and creatinine) and non-nitrogenous waste products that are normally excreted by the kidney, a reduction in urine output, or both. AKI may be categorized as prerenal, intrinsic renal, or postrenal in causation. Intrinsic renal disease can be further divided into glomerular, tubular, interstitial, and vascular abnormalities. AKI is accompanied by an inflammatory response that if unchecked can lead to renal fibrosis and chronic renal failure. AKI usually occurs over a period of hours or days and is potentially reversible. AKI may be characterized as an abrupt (i.e., for example, within 14 Days, within 7 Days, within 72 hours, or within 48 hours) reduction in kidney function identified by an absolute increase in serum creatinine of greater than or equal to 0.3 mg/dl (≥26.4 μmol/l), a percentage increase in serum creatinine of greater than or equal to 50% (1.5-fold from baseline), or a reduction in urine output (documented oliguria of less than 0.5 ml/kg per hour for at least 6 hours). Risk factors include, for example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin. This list is not meant to be limiting.

The term "kidney malfunction" as used herein is intended to include kidney disorders, kidney disease, kidney dysfunction, kidney cancer, absence of at least one kidney due to accidents, surgical removal or genetic disorders, or other conditions where one or both of the kidneys are not properly functioning. The term kidney malfunction may include acute kidney injury.

The term "thrombosis" as used herein in its conventional sense refers to a clotting disorder to which an excess of platelets contributes. Thrombosis may refer to the formation of a thrombus (blood clot) inside a blood vessel. The term encompasses, without limitation, arterial and venous thrombosis, including deep vein thrombosis, portal vein thrombosis, jugular vein thrombosis, renal vein thrombosis, stroke, myocardial infarction, Budd-Chiari syndrome, Paget-Schroetter disease, and cerebral venous sinus thrombosis. In some embodiments, the patient is at heightened risk relative to the general population (e.g., as measured by recognized risk factors) of a thrombotic event. In some embodiments, a patient has one or more risk factors that make the patient have a high risk of developing thrombosis relative to the general population. Risk factors for thrombosis include, e.g., classical cardiovascular disease risk factors: hyperlipidemia, smoking, diabetes, hypertension, and abdominal obesity; strong classical venous thromboembolism risk factors: trauma or fractures, major orthopedic surgery, and oncological surgery; moderate classical venous thromboembolism risk factors: non-oncological surgery, oral contraceptives and hormone replacement therapy, pregnancy and puerperium, hypercoagulability, and previous venous thromboembolism; and weak classical venous thromboembolism risk factors: age, bed rest (>3 days), prolonged travel, and metabolic syndrome. Additional risk factors include inherited, acquired and mixed coagulation or metabolic risk factors for thrombosis such as, e.g., inherited: antithrombin deficiency, protein C deficiency, Protein S deficiency, Factor V Leiden, Prothrombin G20210A; acquired: antiphospholipid syndrome; mixed: hyperhomocysteinaemia, increased fibrinogen levels, increased factor VIII levels, increased factor IX levels. In some cases, the use of heparin may increase the risk of thrombosis including, e.g., heparin-induced thrombocytopenia (HIT). Diseases and conditions associated with thrombosis include, without limitation, acute venous thrombosis, pulmonary embolism, thrombosis during pregnancy, hemorrhagic skin necrosis, acute or chronic disseminated intravascular coagulation (DIC), sepsis induced coagulopathy (SIC), clot formation from surgery, long bed rest, long periods of immobilization, venous thrombosis, fulminant meningococcomia, acute thrombotic stroke, acute coronary occlusion, acute peripheral arterial occlusion, massive pulmonary embolism, axillary vein thrombosis, massive iliofemoral vein thrombosis, occluded arterial cannulae, occluded venous cannulae, cardiomyopathy, venoocclusive disease of the liver, hypotension, decreased cardiac output, decreased vascular resistance, pulmonary hypertension, diminished lung compliance, leukopenia, thrombocytopenia (e.g., immune thrombocytopenia), and immune thrombocytic purpura. in a subject at risk for thrombosis, the subject may be monitored using methods known to those of skill in the art of maintaining hemostasis in patients at risk for thrombosis. Examples of methods for monitoring patients at risk of thrombosis included, without limitation, digital subtraction angiography, in vitro assays or non-invasive methods. Examples of in vitro assays useful for identifying and monitoring subjects at risk for thrombosis and for treatment using the present methods include, without limitation, functional assays and antibody detection assays.

The term, "thrombotic event," includes, but is not limited to, thrombotic disorders such as myocardial infarction, unstable angina, stroke, pulmonary embolism, transient ischemic attack, deep vein thrombosis, thrombotic re-occlusion and peripheral vascular thrombosis. A thrombotic event also includes thrombotic re-occlusion which occurs subsequent to a coronary intervention procedure or thrombolytic therapy. The term, "thrombotic event," means any disorder which involves a blockage or partial blockage of an artery or vein with a thrombosis.

The term "COVID-19" refers to a coronavirus COVID-19 (previously known as 2019-nCoV) which first appeared in Wuhan, China.

The term "COVID-19-associated ARDS" refers to ARDS that is caused by COVID-19 infection. Patients having COVID-19-associated ARDS may have been diagnosed as having a COVID-19 infection, may have been exposed to another person having a COVID19 infection, or may be suspected of having a COVID-19 infection based on their symptoms.

The term "COVID-19-associated AKI" refers to AKI that is caused by COVID-19 infection. Patients having COVID-19-associated AKI may have been diagnosed as having a COVID-19 infection, may have been exposed to another person having a COVID-19 infection, or may be suspected of having a COVID-19 infection based on their symptoms. In some cases, COVID-19-associated AKI includes AKI with the symptoms described, e.g., in Batlle et al. J. AM. SOC. NEPHROL. 2020, 31(7): 1380-1383 and Gabarre et al. Intensive Care Med. 2020, 46(7): 1339-1348, the disclosures of which are incorporated herein by reference in their entireties.

The term "COVID-19-associated thrombosis" refers to thrombosis that is caused by COVID-19 infection. Patients having COVID-19-associated thrombosis may have been diagnosed as having a COVID-19 infection, may have been exposed to another person having a COVID-19 infection, or may be suspected of having a COVID-19 infection based on their symptoms. In some cases, COVID-19-associated thrombosis includes any of the symptoms described in, e.g., Connors et al. Blood 2020, 135(23): 2033-2040 and Bikdeli et al. J. Am. Coll. Cardiol. 2020, 75(23): 2950-73, the disclosures of which are incorporated herein by reference in their entireties.

The term "associated with COVID-19" refers to a symptom or indication that develops within 28 days of hospitalization/signs of COVID-19 infection.

The term "treatment" refers to a reduction in symptoms. For COVID-19-associated ARDS, successful treatment may include a decrease in shortness of breath, less labored or less rapid breathing, higher blood pressure, decreased confusion and/or a decrease tiredness. A treatment may be administered prophylactically, i.e., before the onset of ARDS. A prophylactic treatment prevents ARDS and can be administered to patients that have or are suspected of having a COVID-19 infection, but without the severe symptoms of ARDS. For example, prophylactic treatment can be administered to patients that have a cough without the other symptoms of ARDS.

For COVID-19-associated AKI, successful treatment may include increased kidney function. Kidney function may be assessed by measuring serum creatinine levels, serum creatinine clearance, or blood urea nitrogen levels. In some cases, the successful treatment includes a reduction in metabolic acidosis, hyperkalaemia, oliguria or anuria, azotemia, restoration in body fluid balance, and improved effects on other organ systems. A treatment may be administered prophylactically, i.e., before the onset of AKI. A prophylactic treatment prevents AKI and can be administered to patients that have or are suspected of having a COVID-19 infection, but without the severe symptoms of AKI. For example, prophylactic treatment can be administered to patients that have one or more of increased serum or urine creatinine, hematuria, hypoproteinemia, decreased antithrombin III levels, hypalbuminaemia, leucozyturia, or proteinuria without the other symptoms of AKI.

For COVID-19-associated thrombosis, successful treatment may include improvement in the subject's coagulation profile, or preventing, slowing, delaying, or arresting, a worsening of the coagulation profile for which the subject is at risk. A coagulation profile may be assessed by measurement of one or more coagulation parameters including, e.g., a subject's serum level of one or more of D-dimer, Factor II, Factor V (e.g., Factor V Leiden), Factor VII, Factor VIII, Factor IX, Factor XI, Factor XII, Factor XIII, F/fibrin degradation products, thrombin-antithrombin 111 complex, fibrinogen, plasminogen, prothrombin, and von Willebrand factor. Additional coagulation parameters that may be measured for the coagulation profile include, e.g., prothrombin time, thromboplastin time, activated partial thromboplast time (aPTT), antithrombin activity, platelet count, protein C levels, and protein S levels. In addition, the levels of C reactive protein may also be assessed in the patient prior to treatment and if elevated this may be used as a further indicator as to an increased risk of thrombosis in the patient.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. As used herein, "lower alkyl" means (C1-C8) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. As used herein, "lower alkanyl" means (C1-C8) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. As used herein, "lower alkenyl" means (C2-C8) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In some embodiments, the alkyldiyl group is (C1-C8) alkyldiyl. Specific embodiments include saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkyleno group is (C1-C8) or (C1-C3) alkyleno. Specific embodiments include straight-chain saturated alkano groups, e.g., methano, ethano, propano, butano, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C8) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C8) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like.

"Aryl" by itself or as part of another substituent refers to a monovalent aromatic hydrocarbon group having the stated number of carbon atoms (i.e., C6-C15 means from 6 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C6-C15) aryl, with (C6-C10) being more typical. Specific exemplary aryls include phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C6-C15) arylaryl is an arylaryl group in which each aromatic ring comprises from 6 to 15 carbons, e.g., biphenyl, triphenyl, binaphthyl, phenylnaphthyl, etc. In some embodiments, each parent aromatic ring system of an arylaryl group is independently a (C6-C15) aromatic, more preferably a (C6-C10) aromatic. Specific exemplary arylaryl groups include those in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. In some embodiments, the aromatic ring systems are (C6-C15) aromatic rings, more typically (C6-C10) aromatic rings. A particular exemplary biaryl group is biphenyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C7-C21) arylalkyl, e.g., the alkanyl, alkenyl or alkynyl moiety of the arylalkyl group is (C1-C6) and the aryl moiety is (C6-C15). In some specific embodiments the arylalkyl group is (C7-C13), e.g., the alkanyl, alkenyl or alkynyl moiety of the arylalkyl group is (C1-C3) and the aryl moiety is (C6-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Specifically excluded from the definition of "parent heteroaromatic ring system" are benzene rings fused to cyclic polyalkylene glycols such as cyclic polyethylene glycols. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. In some embodiments, each parent heteroaromatic ring system is independently a 5-15 membered heteroaromatic, more typically a 5-10 membered heteroaromatic. Specific exemplary heteroaryl-heteroaryl groups include those in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-15 membered heteroaromatic rings, more typically 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In some specific exemplary embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Substituted," when used to modify a specified group or radical, means that one or more hydrogen atoms of the specified group or radical are each, independently of one another, replaced with the same or different substituent(s). Substituent groups useful for substituting for hydrogens on saturated carbon atoms in the specified group or radical include, but are not limited to —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}C(O)O^-M^+$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of alkyl, cycloalkyl, heteroalkyl, cycloheteroalkyl, aryl, arylalkyl, heteroaryl and heteroarylalkyl; each $R^{70}$ is independently hydrogen or $R^{60}$; each $R^{80}$ is independently $R^{70}$ or alternatively, the two $R^{80}$'s, taken together with the nitrogen atom to which they are bonded, form a 5-, 6- or 7-membered cycloheteroalkyl which may optionally include from 1 to 4 of the same or different additional heteroatoms selected from the group consisting of O, N and S; and each $M^+$ is a counter ion with a positive charge, for example, a positive charge independently selected from $K^+$, $Na^+$, $^+N(R^{60})_4$, and $Li^+$, or two of $M^+$, combine to form a divalent counterion, for example a divalent counterion selected from $Ca^{2+}$, $Mg^{2+}$, and $Ba^{2+}$. As specific examples, —$NR^{80}R^{80}$ is meant to include —$NH_2$, —NH-alkyl, N-pyrrolidinyl and N-morpholinyl.

Similarly, substituent groups useful for substituting for hydrogens on unsaturated carbon atoms in the specified group or radical include, but are not limited to, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}C(O)O^-M^+$, —$NR^{70}C(O)OR^{70}$, —$NR^{70}C(S)OR^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups, other than R$^P$, useful for substituting for hydrogens on nitrogen atoms in heteroalkyl and cycloheteroalkyl groups include, but are not limited to, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups from the above lists useful for substituting other groups or atoms specified as "substituted" will be apparent to those of skill in the art.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder.

Methods of Treatment

As noted above, provided herein are a variety of methods that involve administering fostamatinib, a pro-drug thereof or a pharmaceutically acceptable salt thereof to a patient. Also provided are methods for identifying a patient with kidney malfunction, e.g., acute kidney injury, and/or thrombosis (e.g., detecting kidney malfunction and/or thrombosis in a patient) and administering fostamatinib, a pro-drug thereof or a pharmaceutically acceptable salt thereof to the patient. The methods may include a step (a) of testing a patient for kidney malfunction (e.g., acute kidney injury) and/or thrombosis, e.g., before any treatment including fostamatinib, a pro-drug thereof or a pharmaceutically acceptable salt thereof is administered. The methods may then include step (b) of administering fostamatinib, a pro-drug thereof or a pharmaceutically acceptable salt thereof to the patient according to any of the embodiments described herein.

In some embodiments, the method may comprise administering fostamatinib, a pro-drug thereof or a pharmaceutically acceptable salt thereof to a patient having or suspected of having a COVID-19 infection. In some embodiments, the method may comprise administering fostamatinib, a pro-drug thereof or a pharmaceutically acceptable salt thereof to a patient having, suspected of having or expected to develop acute respiratory distress syndrome. In some embodiments, the method may comprise administering fostamatinib, a pro-drug thereof or a pharmaceutically acceptable salt thereof to a patient having, suspected of having or expected to develop symptoms associated with a cytokine response. In some embodiments, the symptoms are associated with acute respiratory distress syndrome and/or acute kidney injury. In some embodiments, the method may comprise administering fostamatinib, a pro-drug thereof or a pharmaceutically acceptable salt thereof to a patient having, suspected of having or expected to develop acute kidney injury. In some embodiments, the method may comprise administering fostamatinib, a pro-drug thereof or a pharmaceutically acceptable salt thereof to a patient having, suspected of having or expected to develop thrombosis.

As summarized above, aspects of the methods may include identifying a patient with kidney malfunction and/or thrombosis (e.g., detecting kidney malfunction and/or thrombosis in a patient) and administering fostamatinib, a pro-drug thereof or a pharmaceutically acceptable salt thereof to the patient. The methods may include step (a) of testing a patient for kidney malfunction and/or thrombosis. The testing may occur before any treatment including fostamatinib, a pro-drug thereof or a pharmaceutically acceptable salt thereof is administered. Exemplary tests for identifying patients with kidney malfunction include urine tests and blood tests (e.g., to examine creatinine levels and ACR (albumin to creatinine ratio) and estimate GFR (glomerular filtration rate)), blood urea nitrogen (BUN) tests, kidney tissue biopsies, and kidney imaging tests (e.g., ultrasound scan, MRI scan, CT scan). Exemplary tests for identifying patients with thrombosis include imaging tests (e.g., ultrasound scan, MRI scan, CT scan, duplex ultrasonography), blood test (e.g., a D-dimer test), venography, computed tomographic pulmonary angiography, ventilation-perfusion (V/Q) scan, and pulmonary angiography. In some embodiments, step (a) may produce or provide one or more test results indicating the patient has, is suspected of having or is expected to develop kidney malfunction and/or thrombosis. In some cases, the methods may include determining the patient has, is suspected of having or is expected to develop acute kidney injury and/or thrombosis based on the one or more results from step (a). In some cases, step (a) or the results of step (a) reveal that a patient has, is suspected of having or is expected to develop acute kidney injury and/or thrombosis. The methods may then include step (b) of administering fostamatinib, a pro-drug thereof or a pharmaceutically acceptable salt thereof to a patient that has been identified based on the results of step (a) as having kidney malfunction and/or thrombosis. The administering may occur according to any of the embodiments described herein.

Figure 2:
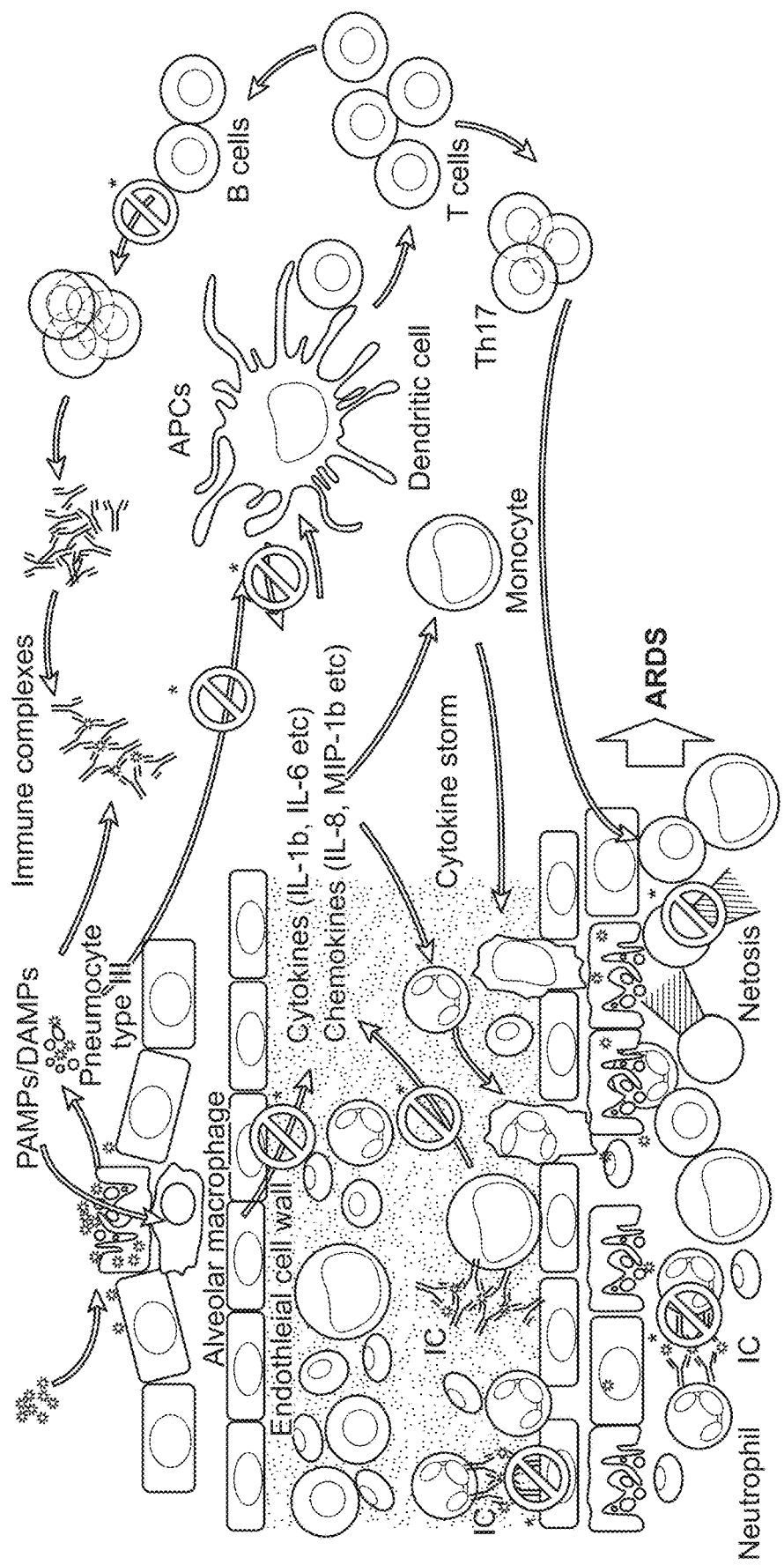
FIG. 2 shows embodiments of targets (*) of fostamatinib including CLEC-dependent cytokine release by innate immune cells, immune complex driven Fc receptor mediated monocyte or endothelial cell activation, and neutrophil activation and NETosis.

In some cases, fostamatinib modulates, e.g., increases or decreases or inhibits, signaling pathways associated with COVID-19 infection. For example, fostamatinib, a SYK inhibitor, may modulate, e.g., inhibit, immune cell activation by tissue damage (DAMP) or pathogen (PAMP) signals via C-type lectin receptors (CLRs) and by antibody-antigen immune complexes via Fc receptors (FcRs), both of which are involved in COVID19 pathogenesis (FIG. 1). In some cases, fostamatinib modulates a CLEC-driven cytokine storm associated with COVID-19 infection (FIG. 2). In some cases, fostamatinib modulates FcγR driven ARDS associated with COVID-19 infection (FIG. 2). In some cases, fostamatinib modulates FcγRIIA, CLEC2 and GPVI signaling involved in COVID-19-associated thrombosis. In some cases, fostamatinib modulates FcγRIIA-mediated NETosis of neutrophils in COVID-19-associated thrombosis. In some cases, fostamatinib modulates COVID-19 associated thrombosis without affecting normal hemostasis, and in such embodiments, fostamatinib may target receptors involved in thrombosis but non-essential for hemostasis. For example, in some embodiments, fostamatinib may inhibit FcγRIIa-mediated platelet aggregation, GPVI-mediated platelet aggregation, and/or CLEC2-mediated platelet aggregation and may not affect ADP-mediated platelet aggregation.

In any embodiment, the patient may have or may be expected to have or develop acute respiratory distress syndrome. In some cases, however, the patient may have signs of respiratory distress, e.g., a cough, but does not have acute respiratory distress syndrome. In these embodiments, the patient may not be in intensive care.

In some embodiments, the patient may have or may be expected to have or develop acute kidney injury. In some cases, the patient may have signs of kidney damage or injury including, e.g., proteinuria, hematuria, kaliuresis, albuminuria, oliguria, increased blood urea nitrogen, and/or an increase in serum creatinine. In some cases, however, the patient may have signs of reduced kidney function or kidney malfunction such as, e.g., proteinuria, hematuria, changes (e.g., increase) in serum creatinine (sCr) and/or blood urea nitrogen, decreased urine output, etc. In some cases, however, the patient may have signs of reduced kidney function or kidney malfunction but does not have acute kidney injury. In these embodiments, the patient may not be in intensive care.

In some embodiments, the patient may have or may be expected to have or develop thrombosis. In some cases, the patient may have signs of thrombosis including, e.g., pain and swelling, warm skin, red or darkened skin, cyanosis, swollen veins, shortness of breath, irregular heartbeat, chest pain, lightheadedness, sweating, coughing (e.g., cough that produces blood), and/or low blood pressure. In some case, the patient may have a prothrombotic coagulation profile but does not have thrombosis. In some case, the patient may have a prothrombotic coagulation profile and has or is expected to have thrombosis. The prothrombotic coagulation profile may include a worsening, e.g., an increase or decrease in the level or activity, of one or more of any of the coagulation parameters as described herein, e.g., compared to a control. For example, in some cases, the prothrombotic coagulation profile may include increased levels of D-dimer. The control may be, e.g., the coagulation profile of an asymptomatic individual with a COVID-19 infection, an individual with a mild COVID-19 infection, or a healthy individual. In these embodiments, the patient may not be in intensive care.

In any embodiment, the patient may be at least 60 years old, at least 70 years old, or at least 80 years old. The patient may have or may have had one or more other lung diseases in the past. For example, in some cases, the patient has or has a history of having asthma, pneumothorax, atelectasis, bronchitis, chronic obstructive pulmonary disease, lung cancer or pneumonia.

In some cases, the patient may have or may have had one or more other kidney diseases in the past. In some embodiments, kidney diseases comprise acromegaly, acute renal failure (ARF) amyloidosis, autosomal dominant polycystic kidney disease, kidney stones, kidney cysts, autosomal recessive polycystic kidney disease, chronic renal failure (CRF), chronic renal disease, coffin-Lowry syndrome, cor pulmonale, cryoglobulinemia, diabetic nephropathy, dyslipidemia, Gaucher disease, glomerulonephritis, goodpasture syndrome, hemolytic uremic syndrome, hepatitis, kidney cancer, kidney stones, leukemia, lipoproteinemia, lupus, multiple myeloma, nephritis, polyartekidney cysts, post streptococcal glomerulonephritis, glomerulonephritis, kidney pain, preeclampsia, renal tuberculosis, pyelonephritis, renal tubular acidosis kidney disease, streptococcal toxic shock syndrome, thromboembolism, toxoplasmosis, urinary tract infections, vesicoureteral reflux, or williams syndrome. In one embodiment, the kidney disease or disorder is acute, or in another embodiment, chronic. In one embodiment, the phrase "predisposed to a kidney disease or disorder" with respect to a subject is synonymous with the phrase "subject at risk", and includes a subject at risk of acute or chronic renal failure, or at risk of the need for renal replacement therapy, if the subject is reasonably expected to suffer a progressive loss of renal function associated with progressive loss of functioning nephron units. Whether a particular subject is at risk is a determination which may routinely be made by one of ordinary skill in the relevant medical or veterinary art. In some cases, the patient has or has a history of having dialysis treatments. In some cases, the patient has had a kidney transplant.

In some cases, the patient may have or may have had thrombosis or a thrombotic event in the past. For example, in some cases, the patient has or has a history of having any of the risk factors, diseases, or conditions associated with thrombosis described herein including, e.g., deep vein thrombosis, pulmonary embolism, etc. In some cases, the patient has one or more risk factors for developing thrombosis relative to the general population.

The administering can be done any convenient way. For example, the administration may be systemic, e.g., orally (via injection of tablet, pill or liquid) or intravenously (by injection or via a drip, for example). In other embodiments, the administering can be done by pulmonary administration, e.g., using an inhaler or nebulizer.

Compounds

Compounds that find use in the invention are generally 2,4-pyrimidinediamine compounds according to structural formula (I):

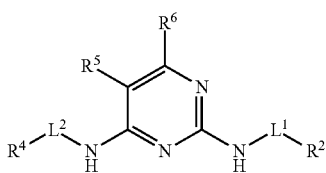

including salts (e.g., pharmaceutically acceptable salts), hydrates, solvates and N-oxides thereof, wherein:

$L^1$ and $L^2$ are each, independently of one another, selected from the group consisting of a direct bond and a linker;

$R^2$ and $R^4$ are as described in the following embodiments and examples;

$R^5$ is selected from the group consisting of $R^6$, (C1-C6) alkyl optionally substituted with one or more of the same or different $R^8$ groups, (C1-C4) alkanyl optionally substituted with one or more of the same or different $R^8$ groups, (C2-C4) alkenyl optionally substituted with one or more of the same or different $R^8$ groups and (C2-C4) alkynyl optionally substituted with one or more of the same or different $R^8$ groups;

each $R^6$ independently is selected from the group consisting of hydrogen, an electronegative group, —$OR^{d1}$, —$SR^{d1}$, (C1-C3) haloalkyloxy, (C1-C3) perhaloalkyloxy, —$NR^cR^c$, halogen, (C1-C3) haloalkyl, (C1-C3) perhaloalkyl, —$CF_3$, —$CH_2CF_3$, —$CF_2CF_3$, —CN, —NC, —OCN, —SCN, —NO, —$NO_2$, —$N_3$, —S(O)$R^{d1}$, —$S(O)_2R^{d1}$, —$S(O)_2OR^{d1}$, —$S(O)NR^cR^c$, —$S(O)_2NR^cR^c$, —$OS(O)R^{d1}$, —$OS(O)_2R^{d1}$, —$OS(O)_2OR^{d1}$, —$OS(O)NR^cR^c$, —$OS(O)_2NR^cR^c$, —$C(O)R^{d1}$, —$C(O)OR^{d1}$, —$C(O)NR^cR^c$, —C(NH)
$NR^cR^c$, —$OC(O)R^{d1}$, —$SC(O)R^{d1}$, —$OC(O)OR^{d1}$, —$SC(O)OR^{d1}$, —$OC(O)NR^cR^c$, —$SC(O)NR^cR^c$, —$OC(NH)NR^cR^c$, —$SC(NH)NR^cR^c$, —$[NHC(O)]_nR^{d1}$, —$[NHC(O)]_nOR^{d1}$, —$[NHC(O)]_mNR^cR^c$ and —$[NHC(NH)]_nNR^cR^c$, (C5-C10) aryl optionally substituted with one or more of the same or different $R^8$ groups, phenyl optionally substituted with one or more of the same or different $R^8$ groups, (C6-C16) arylalkyl optionally substituted with one or more of the same or different $R^8$ groups, 5-10 membered heteroaryl optionally substituted with one or more of the same or different $R^8$ groups and 6-16 membered heteroarylalkyl optionally substituted with one or more of the same or different $R^8$ groups;

$R^8$ is selected from the group consisting of $R^a$, $R^b$, $R^a$ substituted with one or more of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —O—$(CH_2)_m$—$R^b$, —S—$(CH_2)_m$—$R^b$, —O—$CHR^aR^b$, —O—$CR^a(R^b)_2$, —O—$(CHR^a)_m$—$R^b$, —O—$(CH_2)_m$—$CH[(CH_2)_mR^b]$ $R^b$, —S—$(CHR^a)_m$—$R^b$, —$C(O)NH$—$(CH_2)_m$—$R^b$, —$C(O)NH$—$(CHR^a)_m$—$R^b$, —O—$(CH_2)_m$—$C(O)$ $NH$—$(CH_2)_m$—$R^b$, —S—$(CH_2)_m$—$C(O)NH$ —$(CH_2)_m$—$R^b$, —O—$(CHR^a)_m$—$C(O)NH$ —$(CHR^a)_m$—$R^b$, —S—$(CHR^a)_m$—$C(O)NH$— $(CHR^a)_m$—$R^b$, —NH—$(CH_2)_m$—$R^b$, —NH— $(CHR^a)_m$—$R^b$, —$NH[(CH_2)_mR^b]_2$, —$N[(CH_2)_mR^b]_2$, —NH—$C(O)$—NH—$(CH_2)_m$—$R^b$, —NH—$C(O)$— $(CH_2)_m$—$CHR^bR^b$ and —NH—$(CH_2)_m$—$C(O)$— NH—$(CH_2)_m$—$R^b$;

each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from the group consisting of =O, —$OR^{d1}$, (C1-C3) haloalkyloxy, —$OCF_3$, =S, —$SR^{d1}$, =$NR^{d1}$, =$NOR^{d1}$, —$NR^cR^c$, halogen, —$CF_3$, —CN, —NC, —OCN, —SCN, —NO, —$NO_2$, =$N_2$, —$N_3$, —$S(O)R^{d1}$, —$S(O)_2R^{d1}$, —$S(O)_2OR^{d1}$, —$S(O)NR^cR^c$, —$S(O)_2NR^cR^c$, —$OS(O)R^{d1}$, —$OS(O)_2R^{d1}$, —$OS(O)_2OR^{d1}$, —$OS(O)_2NR^cR^c$, —$C(O)R^{d1}$, —$C(O)$ $OR^{d1}$, —$C(O)NR^cR^c$, —$C(NH)NR^cR^c$, —$C(NR^a)$ $NR^cR^c$, —$C(NOH)R^a$, —$C(NOH)NR^cR^c$, —$OC(O)$ $R^{d1}$, —$OC(O)OR^{d1}$, —$OC(O)NR^cR^c$, —$OC(NH)$ $NR^cR^c$, —$OC(NR^a)NR^cR^c$, —$[NHC(O)]_nR^{d1}$, —$[NR^aC(O)]_nR^{d1}$, —$[NHC(O)]_nOR^{d1}$, —$[NRC(O)]_nOR^{d1}$, —$[NHC(O)]_nNR^cR^c$, —$[NR^aC(O)]_n$ $NR^cR^c$, —$[NHC(NH)]_nNR^cR^c$ and —$[NR^aC(NR^c)]_nNR^cR^c$;

each $R^c$ is independently $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which is optionally substituted with one or more of the same or different $R^a$ or suitable $R^b$ groups;

each $R^{d1}$ is independently $R^a$;

each m is independently an integer from 1 to 3; and each n is independently an integer from 0 to 3.

In the compounds of structural formula (I), $L^1$ and $L^2$ represent, independently of one another, a direct bond or a linker. Thus, as will be appreciated by skilled artisans, the substituents $R^2$ and/or $R^4$ may be bonded either directly to their respective nitrogen atoms or, alternatively, spaced away from their respective nitrogen atoms by way of a linker. The identity of the linker is not critical and typical suitable linkers include, but are not limited to, (C1-C6) alkyldiyls, (C1-C6) alkanos and (C1-C6) heteroalkyldiyls, each of which may be optionally substituted with one or more of the same or different $R^8$ groups, where $R^8$ is as previously defined for structural formula (I). In a specific embodiment, $L^1$ and $L^2$ are each, independently of one another, selected from the group consisting of a direct bond, (C1-C3) alkyldiyl optionally substituted with one or more of the same or different $R^a$, suitable $R^b$ or $R^9$ groups and 1-3 membered heteroalkyldiyl optionally substituted with one or more of the same or different $R^a$, suitable $R^b$ or $R^9$ groups, wherein $R^9$ is selected from the group consisting of (C1-C3) alkyl, —$OR^a$, —$C(O)OR^a$, (C5-C10) aryl optionally substituted with one or more of the same or different halogens, phenyl optionally substituted with one or more of the same or different halogens, 5-10 membered heteroaryl optionally substituted with one or more of the same or different halogens and 6 membered heteroaryl optionally substituted with one or more of the same or different halogens; and $R^a$ and $R^b$ are as previously defined for structural formula (I). Specific $R^9$ groups that may be used to substitute $L^1$ and $L^2$ include —$OR^a$, —$C(O)OR^a$, phenyl, halophenyl and 4-halophenyl, wherein $R^a$ is as previously defined for structural formula (I).

In certian embodiments, $L^1$ and $L^2$ are each, independently of one another, selected from the group consisting of methano, ethano and propano, each of which may be optionally monosubstituted with an $R^9$ group, where $R^9$ is as previously defined above.

In certain embodiments, specific $R^a$ groups that may be included in $R^9$ groups are selected from the group consisting of hydrogen, (C1-C6) alkyl, phenyl and benzyl.

In certain embodiments, $L^1$ and $L^2$ are each a direct bond such that the 2,4-pyrimidinediamine compounds of the invention are compounds according to structural formula (Ia):

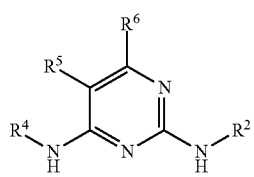

including salts, hydrates, solvates and N-oxides thereof, wherein $R^2$, $R^4$, $R^5$ and $R^6$ are as previously defined for structural formula (I). Additional specific embodiments of the 2,4-pyrimidinediamine compounds of the invention are described below.

In certain embodiments of the compounds of structural formula (I) and (Ia), $L^1$, $L^2$, $R^5$, $R^6$, $R^8$, $R^a$, $R^b$, $R^c$, $R^{d1}$, m and n are as previously defined, $R^2$ is

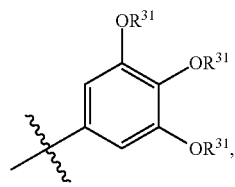

wherein each $R^{31}$, independently of the others, is methyl or (C1-C6) alkyl and $R^4$ is

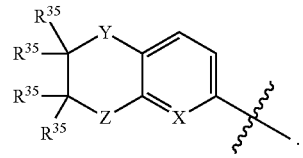

X is selected from the group consisting of N and CH, Y is selected from the group consisting of O, S, SO, $SO_2$, $SONR^{36}$, NH, $NR^{35}$ and $NR^{37}$, Z is selected from the group consisting of O, S, SO, $SO_2$, $SONR^{36}$, NH, $NR^{35}$ and $NR^{37}$. Each $R^{35}$ is, independently of the others, selected from the group consisting of hydrogen and $R^8$, or, alternatively, two $R^{35}$ bonded to the same carbon atom are taken together to form an oxo (=O), NH or $NR^{38}$ group and the other two $R^{35}$ are each, independently of one another, selected from the group consisting of hydrogen and $R^8$. Each $R^{36}$ is independently selected from the group consisting of hydrogen and (C1-C6) alkyl. Each $R^{37}$ is independently selected from the group consisting of hydrogen and a progroup. $R^{38}$ is selected from the group consisting of (C1-C6) alkyl and (C5-C14) aryl.

In particular, Y is O, Z is NH and X is N. $R^5$ can be halogen and $R^6$ is a hydrogen.

In certain embodiments of the compounds of structural formula (I) and (Ia), $L^1$, $L^2$, $R^5$, $R^6$, $R^8$, $R^a$, $R^b$, $R^c$, $R^{d1}$, m, n, $R^{35}$, $R^{36}$, $R^{37}$, $R^{38}$, X, Y and Z are as previously defined, $R^2$ is

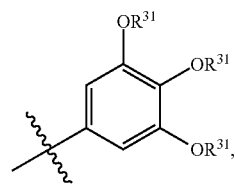

wherein each $R^{31}$, independently of the others, is methyl or (C1-C6) alkyl and $R^4$ is

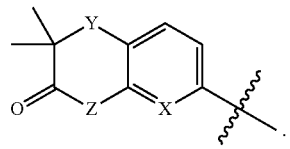

In particular, Y is O, Z is NH and X is N. $R^5$ can be halogen and $R^6$ is a hydrogen. In one particular aspect, Y is O, Z is NH, X is N and each $R^{31}$ is methyl.

In certain embodiments of the compounds of structural formula (I) and (Ia), $L^1$, $L^2$, $R^5$, $R^6$, $R^8$, $R^a$, $R^b$, $R^c$, $R^{d1}$, m, n, $R^{31}$, $R^{35}$, $R^{36}$, $R^{37}$, $R^{38}$, X, Y and Z are as previously defined, $R^2$ is 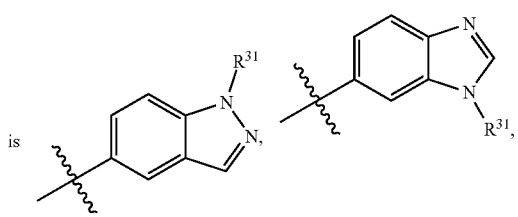

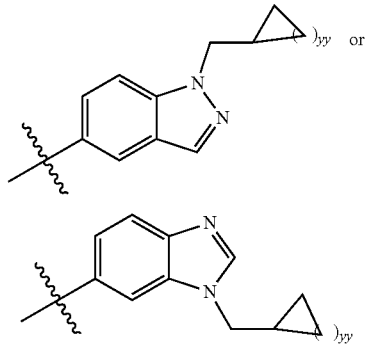

and R⁴ is

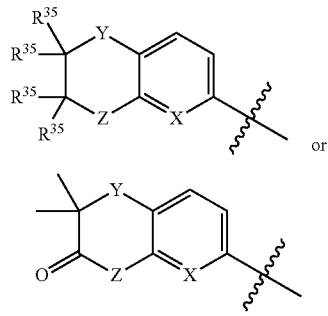

and yy is 1-6. In particular, Y is O, Z is NH and X is N. R⁵ can be halogen and R⁶ is a hydrogen.

In certain embodiments of the compounds of structural formula (I) and (Ia), L¹, L², R⁵, R⁶, R⁸, $R^a$, $R^b$, $R^c$, $R^{d1}$, m, n, R³⁵, R³⁶, R³⁷, R³⁸, X, Y and Z are as previously defined, R² is

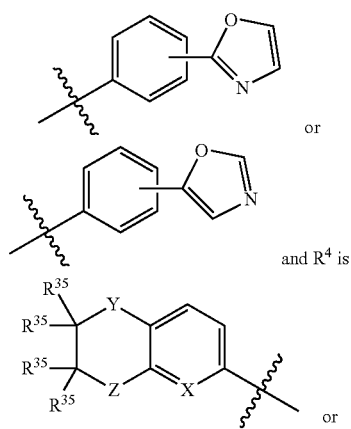

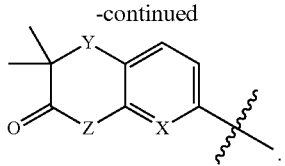

Substitution about the R² phenyl ring can be at the 2, 3, 4, 5 or 6 positions. In particular, Y is O, Z is NH and X is N. R⁵ can be halogen and R⁶ is a hydrogen.

In certain embodiments of the compounds of structural formula (I) and (Ia), L¹, L², R⁵, R⁶, R⁸, $R^a$, $R^b$, $R^c$, $R^{d1}$, m, n, R³⁵, R³⁶, R³⁷, R³⁸, X, Y and Z are as previously defined, R² is a phenyl group disubstituted with two $R^b$ groups and R⁴ is

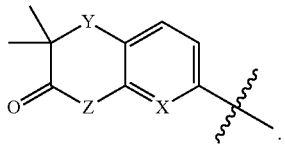

Substitution about the R² phenyl ring can be at the 2,3, 2,4, 2,5, 2,6, 3,4, 3,5, 3,6, 4,5, 4,6 or 5,6 positions, with the proviso that the following compounds are not included:
  N4-(2,2-Dimethyl-3-oxo-4H-5-pyrid[1,4]oxazin-6-yl)-N2-(3-chloro-4-methoxyphenyl)-5-fluoro-2,4-pyrimidinediamine;
  N4-(2,2-Dimethyl-3-oxo-4H-5-pyrid[1,4]oxazin-6-yl)-N2-(3,5-dimethoxyphenyl)-5-fluoro-2,4-pyrimidinediamine;
  N2-(3,4-Dichlorophenyl)-N4-(2,2-dimethyl-3-oxo-4H-5-pyrid[1,4]oxazin-6-yl)-5-fluoro-2,4-pyrimidinediamine;
  N4-(2,2-dimethyl-3-oxo-4H-5-pyrid[1,4]oxazin-6-yl)-N2-(3-fluoro-4-methoxyphenyl)-5-fluoro-2,4-pyrimidinediamine;
  N2-(3,5-Dichlorophenyl)-N4-(2,2-dimethyl-3-oxo-4H-5-pyrid[1,4]oxazin-6-yl)-5-fluoro-2,4-pyrimidinediamine; and
  N2-(3-Chloro-4-trifluoromethoxyphenyl)-N4-(2,2-dimethyl-3-oxo-4H-5-pyrid[1,4]oxazin-6-yl)-5-fluoro-2,4-pyrimidinediamine.

In particular, Y is O, Z is NH and X is N. R⁵ can be halogen and R⁶ is a hydrogen. In certain aspects, each $R^b$ independently is selected from (C1-C6) alkoxy, (C1-16) alkyl, (C1-C6) perhaloalkyls, halogens, carboxylic acid, carboxylic ester, carboxamides, sulfonamides and imidazoles.

In certain embodiments of the compounds of structural formula (I) and (Ia), L¹, L², R⁵, R⁶, R⁸, $R^a$, $R^b$, $R^c$, $R^{d1}$, m, n, R³⁵, R³⁶, R³⁷, R³⁸, X, Y and Z are as previously defined, R² is a phenyl group trisubstituted with three $R^b$ groups and R⁴ is

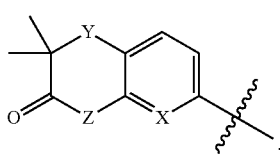

Substitution about the $R^2$ phenyl ring can be at the 2,3,4, 2,3,5, 2,3,6, 2,4,5, 2,4,6, 2,5,6, 3,4,5, 3,4,6, 3,5,6, or 4,5,6 positions, with the proviso that the following compounds are not included:

N2-(3-Chloro-4-methoxy-5-methylphenyl)-N4-(2,2-dimethyl-3-oxo-4H-5-pyrid[1,4]oxazin-6-yl)-5-fluoro-2,4-pyrimidinediamine;

N2-(3-Chloro-4-hydroxy-5-methylphenyl)-N4-(2,2-dimethyl-3-oxo-4H-5-pyrid[1,4]oxazin-6-yl)-5-fluoro-2,4-pyrimidinediamine; and N2-(3,5-Dimethyl-4-methoxyphenyl)-N4-(2,2-dimethyl-3-oxo-4H-5-pyrid[1,4]oxazin-6-yl)-5-fluoro-2,4-pyrimidinediamine.

In particular, Y is O, Z is NH and X is N. $R^5$ can be halogen and $R^6$ is a hydrogen. In certain aspects, each $R^b$ independently is selected from (C1-C6) alkoxy, (C1-16) alkyl, (C1-C6) perhaloalkyls, halogens, carboxylic acid, carboxylic esters, carboxamides, sulfonamides In certain embodiments, $R^5$ of the pyrimidine ring is a halogen atom, such as fluorine, and $R^6$ of the pyrimidine ring is a hydrogen atom.

In certain embodiments, $L^1$ and $L^2$ are covalent bonds for the above-identified embodiments.

Also specifically described are combinations of the above embodiments.

In certain embodiments, the compound is N4-(2,2-Dimethyl-3-oxo-4H-5-pyrid[1,4]oxazin-6-yl)-5-fluoro-N2-(3,4,5-trimethoxyphenyl)-2,4-pyrimidinediamine, or a pharmaceutically acceptable salt thereof.

Other suitable compounds are described in U.S. Pat. No. 7,122,542, the disclosure of which is incorporated herein by reference.

Prodrugs of Compounds

Aspects of the present invention include the 2,4-pyrimidinediamine compounds described herein, which may include functional groups that can be masked with progroups to create prodrugs. Such prodrugs are usually, but need not be, pharmacologically inactive until converted into their active drug form. Indeed, many of the active 2,4-pyrimidinediamine compounds include promoieties that are hydrolyzable or otherwise cleavable under conditions of use. Prodrugs of the present invention may include an active component, where the active component is a 2,4-pyrimidinediamine compound as described herein.

In the prodrugs of the invention, any available functional moiety may be masked with a progroup to yield a prodrug. Functional groups within the 2,4-pyrimidinediamine compounds that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs of the invention.

The prodrugs generally comprise a biologically active 2,4-pyrimidinediamine compound that is substituted at the nitrogen atom of one or more primary or secondary amine groups with a progroup $R^P$ that metabolizes or otherwise transforms under conditions of use to yield the active 2,4-pyrimidinediamine. In some embodiments, the progroup $R^P$ is a phosphorous-containing progroup. In some embodiments, the progroup includes a group or moiety that is metabolized under the conditions of use to yield an unstable α-hydroxymethyl, α-aminomethyl or α-thiomethyl intermediate, which then further metabolized in vivo to yield the active 2,4-pyrimidinediamine drug. In some embodiments, the progroup includes an α-hydroxyalkyl, α-aminoalkyl or α-thioalkyl moiety, for example an α-hydroxymethyl, α-aminomethyl, α-thiomethyl moiety, that metabolizes under the conditions of use to yield the active 2,4 pyrimidinediamine drug. For example, in some embodiments the progroup $R^P$ is of the formula —$CR^dR^d$—$AR^3$, where each $R^d$ is, independently of the other, selected from hydrogen, cyano, optionally substituted (C1-C20) alkyl, (C1-C20) perfluoroalkyl, optionally substituted (C7-C30) arylalkyl and optionally substituted 6-30 membered heteroarylalkyl, where each optional substituent is, independently of the others, selected from hydrogen, alkyl, aryl, arylalkyl, heteroaryl and heteroalkyl, or, alternatively, the two $R^d$ are taken together with the carbon atom to which they are bonded to form a cycloalkyl containing from 3 to 8 carbon atoms; A is selected from O, S and $NR^{50}$, where $R^{50}$ is selected from hydrogen, alkyl, aryl, arylalkyl, heteroaryl, heteroarylalkyl and cycloheteroalkyl, or alternatively is combined with $R^3$, and, together with the nitrogen to which they are attached, form a three to seven membered ring; and $R^3$ represents a group that can be metabolized in vivo to yield a group of the formula —$CR^dR^d$—AH, where $R^d$ and A are as previously defined.

The identity of $R^3$ is not critical, provided that it can be metabolized under the desired conditions of use, for example under the acidic conditions found in the stomach and/or by enzymes found in vivo, to yield a group of the formula —$CR^dR^d$—AH, where A and $R^d$ are as previously defined. Thus, skilled artisans will appreciate that $R^3$ can comprise virtually any known or later-discovered hydroxyl, amine or thiol protecting group. Non-limiting examples of suitable protecting groups can be found, for example, in *Protective Groups in Organic Synthesis*, Greene & Wuts, 2nd Ed., John Wiley & Sons, New York, 1991 (especially pages 10-142 (alcohols, 277-308 (thiols) and 309-405 (amines) the disclosure of which is incorporated herein by reference).

In a specific embodiment, $R^3$ includes, together with A, an ether, a thioether, a silyl ether, a silyl thioether, an ester, a thioester, an amide, a carbonate, a thiocarbonate, a carbamate, a thiocarbamate, or a urea linkage, —$OCH_2SO_3R$, where R is hydrogen, alkyl, aryl, arylalkyl or a metal salt (e.g., sodium, lithium, potassium); —$GCH_2^+N(R^{51})_3M$, where G is absent, —$OPO_3$—, —$OSO_3$— or —$CO_2$—, $R^{51}$ is hydrogen, alkyl, aryl, arylalkyl, cycloheteroalkyl or cycloheteroalkylalkyl and M— is a counterion, usually a halide ion or the like (acetate, sulfate, phosphate, etc.). Specific exemplary embodiments include, but are not limited to, progroups $R^P$ in which $R^3$ is selected from $R^f$, —$C(O)R^f$, —$C(O)OR^f$, —$C(O)NR^fR^f$ and —$SiR^fR^fR^f$, where each $R^f$ is, independently of the others, selected from hydrogen, optionally substituted lower alkyl, optionally substituted lower heteroalkyl, optionally substituted lower cycloalkyl, optionally substituted lower heterocycloalkyl, optionally substituted (C6-C10) aryl, optionally substituted 5-10 membered heteroaryl, optionally substituted (C7-C18) arylalkyl and optionally substituted 6-18 membered heteroarylalkyl. In a specific embodiment, each $R^f$ is the same.

The identity of the progroup(s) $R^P$ can be selected to tailor the water-solubility and other properties of the underlying active 2,4-pyrimidinediamine compound to be optimized for a particular mode of administration. It can also be selected to provide for removal at specified organs and/or tissues within the body, such as, for example, in the digestive tract, in blood and/or serum, or via enzymes residing in specific organs, such as the liver.

In some embodiments, progroups $R^P$ that are phosphorous-containing progroups include phosphate moieties that can be cleaved in vitro by enzymes such as esterases, lipases and/or phosphatases. Such enzymes are prevalent throughout the body, residing in, for example, the stomach and digestive tract, blood and/or serum, and in virtually all tissues and organs. Such phosphate-containing progroups $R^P$ will generally increase the water-solubility of the underlying active 2,4-pyrimidinediamine compound, making such phosphate-containing prodrugs ideally suited for modes of administration where water-solubility is desirable, such as, for example, oral, buccal, intravenous, intramuscular and ocular modes of administration.

In some embodiments, each phosphate-containing progroup $R^P$ in the prodrug is of the formula —$(CR^dR^d)_y$—O—P(O)(OH)(OH), or a salt thereof, wherein $R^d$ is as previously defined and y is an integer ranging from 1 to 3, typically 1 or 2. In one specific embodiment, each $R^d$ is, independently of the others, selected from hydrogen, substituted or unsubstituted lower alkyl, substituted or unsubstituted phenyl, substituted or unsubstituted methyl and substituted or unsubstituted benzyl. In another specific embodiment, each $R^d$ is, independently of the others, selected from hydrogen and unsubstituted lower alkyl. Specific exemplary phosphate-containing progroups $R^P$ include —CH$_2$—O—P(O)(OH)(OH) and —CH$_2$CH$_2$—O—P(O)(OH)(OH) and/or the corresponding salts.

While not intending to be bound by any theory of operation, when y is 1 in the exemplary phosphate-containing progroups $R^P$, it is believed that the phosphate-containing prodrugs are converted in vivo by enzymes such as phosphatases, lipases and/or esterases to the corresponding hydroxymethylamines, which are then further metabolized in vivo by the elimination of formaldehyde to yield the active 2,4-pyrimidinediamine drug compound. The phosphate and formaldehyde metabolic by-products are innocuous.

When y is 2 in the exemplary phosphate-containing prodrugs, it is believed that the prodrugs are metabolized to the active 2,4-pyrimidinediamine drug compound in vivo by elimination of enol phosphate, which further metabolizes to acetaldehyde and phosphate. The phosphate and acetaldehyde metabolic by-products are innocuous.

Skilled artisans will appreciate that certain types of precursors can be converted in vivo to phosphate groups. Such precursors include, by way of example and not limitation, phosphate esters, phosphites and phosphite esters. For example, phosphites can be oxidized in vivo to phosphates. Phosphate esters can be hydrolyzed in vivo to phosphates. Phosphite esters can be oxidized in vivo to phosphate esters, which can in turn be hydrolyzed in vivo to phosphates. As a consequence of the ability of these phosphate precursor groups to convert to phosphates in vivo, the prodrugs can also include progroups that comprise such phosphate precursors. In some embodiments, the phosphate precursor groups may be directly metabolized to the active 2,4-pyrimidinediamine drug, without first being converted into a phosphate prodrug. In other embodiments, prodrugs comprising progroups that include such phosphate precursors are first metabolized into the corresponding phosphate prodrug, which then metabolizes to the active 2,4-pyrimidinediamine drug via a hydroxymethylamine, as discussed above.

In some embodiments, such phosphate precursor groups are phosphate esters. The phosphate esters can be acyclic or cyclic, and can be phosphate triesters or phosphate diesters. Such esters are generally less water-soluble than the corresponding phosphate acid prodrugs and the corresponding active 2,4-pyrimidinediamine compounds, and are therefore typically suitable for modes of delivering prodrugs of active 2,4-pyrimidinediamine compounds where low water-solubility is desired, including, by way of example and not limitation, administration via inhalation. The solubility of the prodrug can be specifically tailored for specific modes of administration by appropriate selection of the number and identity(ies) of the esterifying groups in the phosphate ester.

The mechanism by which the phosphate ester group metabolizes to the corresponding phosphate group can be controlled by appropriate selection of the esterifying moieties. For example, it is well-known that certain esters are acid (or base) labile, generating the corresponding phosphate under the acidic conditions found in the stomach and digestive tract. In instances where it is desirable for the phosphate ester prodrug to metabolize to the corresponding phosphate prodrug in the digestive tract (such as, for example, where the prodrugs are administered orally), phosphate ester progroups that are acid-labile can be selected. Other types of phosphate esters are acid and base stable, being converted into the corresponding phosphates via enzymes found in certain tissues and organs of the body (see, e.g., the various cyclic phosphate esters described in Erion et al., 2004, J. Am. Chem. Soc. 126:5154-5163, incorporated herein by reference). In instances where it is desirable to convert a phosphate ester prodrug into the corresponding phosphate prodrug within a desired target tissue or site within the body, phosphate esters having the desired metabolic properties can be selected.

In some embodiments, each phosphate ester-containing progroup $R^P$ in the prodrug is an acyclic phosphate ester of the formula —$(CR^dR^d)_y$—O—P(O)(OH)(OR$^e$) or —$(CR^dR^d)_y$—O—P(O)(OR$^e$)(OR$^e$), or a salt thereof, wherein each $R^e$ is, independently of the others, selected from substituted or unsubstituted lower alkyl, substituted or unsubstituted (C6-C14) aryl (e.g., phenyl, naphthyl, 4-loweralkoxyphenyl, 4-methoxyphenyl), substituted or unsubstituted (C7-C20) arylalkyl (e.g., benzyl, 1-phenylethan-1-yl, 2-phenylethan-1-yl), —$(CR^dR^d)_y$—OR$^f$, —$(CR^dR^d)_y$—O—C(O)R$^f$, —$(CR^dR^d)_y$—O—C(O)OR$^f$, —$(CR^dR^d)_y$—S—C(O)R$^f$, —$(CR^dR^d)_y$—S—C(O)OR$^f$, —$(CR^dR^d)_y$—NH—C(O)R$^f$, —$(CR^dR^d)_y$—NH—C(O)OR$^f$ and —Si(R$^d$)$_3$, wherein $R^d$, $R^f$ and y are as defined above. In a specific embodiment, each $R^d$ is selected from hydrogen and unsubstituted lower alkyl and/or each $R^e$ is an unsubstituted lower alkanyl or benzyl. Specific exemplary phosphate ester progroups include, but are not limited to, —CH$_2$—O—P(O)(OH)(OR$^e$), —CH$_2$CH$_2$—O—P(O)(OH)(OR$^e$), —CH$_2$—O—P(O)(OR$^e$)(OR$^e$) and —CH$_2$CH$_2$—O—P(O)(OR$^e$)(OR$^e$), where $R^e$ is selected from lower alkanyl, i-propyl and t-butyl.

In other embodiments, each phosphate ester-containing progroup $R^P$ is a cyclic phosphate ester of the formula

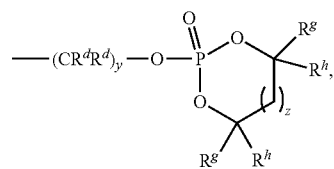

where each $R^g$ is, independently of the others, selected from hydrogen and lower alkyl; each $R^h$ is, independently of the others, selected from hydrogen, substituted or unsubstituted lower alkyl, substituted or unsubstituted lower cycloheteroalkyl, substituted or unsubstituted (C6-C14) aryl, substituted or unsubstituted (C7-C20) arylalkyl and substituted or unsubstituted 5-14 membered heteroaryl; z is an integer ranging from 0 to 2; and $R^d$ and y are as previously defined. In a specific embodiment, each phosphate ester-containing progroup $R^P$ is a cyclic phosphate ester of the formula

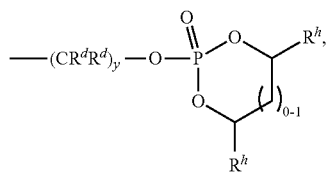

where $R^d$, $R^h$ and y are as previously defined.

The mechanism by which cyclic phosphate ester prodrugs including such cyclic phosphate ester progroups metabolize in vivo to the active drug compound depends, in part, on the identity of the $R^h$ substitutent. For example, cyclic phosphate ester progroups in which each $R^h$ is, independently of the others, selected from hydrogen and lower alkyl are cleaved in vivo by esterases. Thus, in some embodiments, the cyclic phosphate ester progroups are selected such that they are cleavable in vivo by esterases. Specific examples of such cyclic phosphate ester progroups include, but are not limited to, progroups selected from

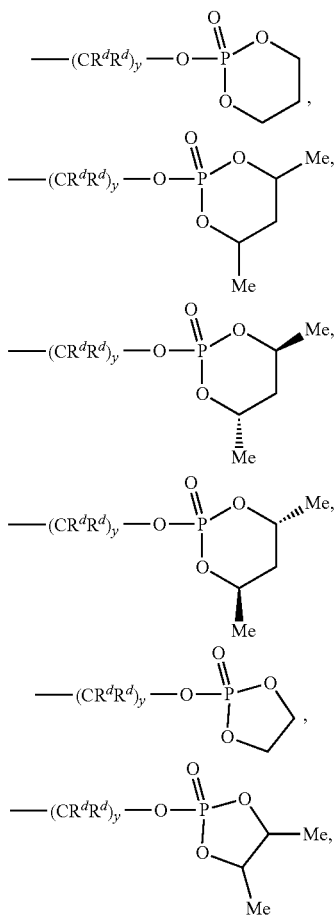

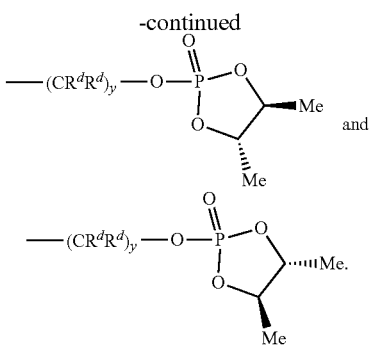

Alternatively, cyclic phosphate ester prodrugs having progroups in which the $R^h$ substituents are substituted or unsubstituted aryl, arylalkyl and heteroaryl groups, are not typically cleaved by esterases, but are instead metabolized to the active prodrug by enzymes, such as cytochrome $P_{450}$ enzymes, that reside in the liver. For example, a series of cyclic phosphate ester nucleotide prodrugs that undergo an oxidative cleavage reaction catalyzed by a cytochrome $P_{450}$ enzyme (CYP) expressed predominantly in the liver are described in Erion et al., 2004, J. Am. Chem. Soc. 126: 5154-5163. In some embodiments, the cyclic phosphate ester progroups are selected such that they are cleavable by CYP enzymes expressed in the liver. Specific exemplary embodiments of such cyclic phosphate ester-containing progroups $R^P$ include, but are not limited to, progroups having the formula

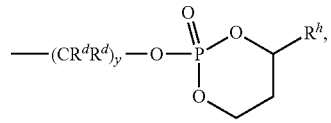

where $R^h$ is selected from phenyl, 3-chlorophenyl, 4-pyridyl and 4-methoxyphenyl.

As skilled artisans will appreciate, phosphites and phosphite esters can undergo oxidation in vivo to yield the corresponding phosphate and phosphate ester analogs. Such reactions can be carried out in vivo by, for example, oxidase enzymes, oxoreductase enzymes and other oxidative enzymes. Thus, the phosphorous-containing progroups $R^P$ can also include phosphite and phosphite ester analogs of any of the phosphate and phosphate ester progroups described above. In some embodiments the phosphorous-containing progroups $R^P$ include, but are not limited to, groups of the formula —$(CR^dR^d)_y$—O—P(OH)(OH), —$(CR^dR^d)_y$—O—P(OH)(OR$^e$) and —$(CR^dR^d)_y$—O—P(OR$^e$)(R$^e$), or salts thereof, where $R^d$, $R^e$ and y are as previously defined. Specific exemplary embodiments include groups in which each $R^d$ is, independently of the others, selected from hydrogen and unsubstituted lower alkyl and/or each $R^e$ is, independently of the others, selected from unsubstituted lower alkanyl and benzyl. Specific exemplary acyclic phosphite and phosphite-ester progroups include, but are not limited to, —CH$_2$—O—P(OH)(OH), —CH$_2$CH$_2$—O—P(OH)(OH), —CH$_2$—O—P(OH)(OR$^e$), and —CH$_2$CH$_2$—O—P(OR$^e$)(OR$^e$), where each $R^e$ is selected from lower alkanyl, i-propyl and t-butyl. Specific exemplary cyclic phosphite ester prodrugs include phosphite analogs of the above-described cyclic phosphate ester progroups. Conceptually, prodrug compounds including such phosphite and/or phosphite ester progroups can be thought of as prodrugs of the corresponding phosphate and phosphate ester prodrugs.

As mentioned above, it is believed that certain phosphate-containing prodrugs metabolize in vivo through the corresponding hydroxymethylamines. Although these hydroxymethylamines metabolize in vivo to the corresponding active 2,4-pyrimidinediamine compounds, they are stable at pH 7 and can be prepared and administered as hydroxyalkyl-containing prodrugs. In some embodiments, each hydroxyalkyl-containing progroup $R^P$ of such prodrugs is of the formula —$CR^dR^d$—OH, where $R^d$ is as previously defined. A specific exemplary hydroxyalkyl-containing progroup $R^P$ is —$CH_2OH$.

Suitable active 2,4-pyrimidinediamine compounds are described, for example, in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005/0234049), and international application Serial No. PCT/US2004/24716, the disclosures of which are incorporated herein by reference. In such 2,4-pyrimidinediamine compounds, the progroup(s) $R^P$ can be attached to any available primary or secondary amine, including, for example, the N2 nitrogen atom of the 2,4-pyrimidinediamine moiety, the N4 nitrogen atom of the 2,4-pyrimidinediamine moiety, and/or a primary or secondary nitrogen atom included in a substituent on the 2,4-pyrimidinediamine compound. The use of phosphate-containing progroups $R^P$ is especially useful for 2,4-pyrimidinediamine compounds that exhibit poor water solubility under physiological conditions (for example, solubilities of less than about 10 μg/ml). While not intending to be bound by any theory of operation, it is believed that the phosphate-containing progroups aid the solubility of the underlying active 2,4-pyrimidinediamine compound, which in turn increases its bioavailability when administered orally. It is believed that the phosphate progroups $R^P$ are metabolized by phosphatase enzymes found in the digestive tract, permitting uptake of the underlying active drug.

It has been discovered that the water solubility and oral bioavailability of a particular biologically active 2,4-pyrimidinediamine compound, illustrated below (Compound 1), increased dramatically when formulated to include a progroup $R^P$ of the formula —$CH_2$—O—$P(O)(OH)_2$ at the ring nitrogen atom highlighted with the asterisk (Compound 4):

Compound 1

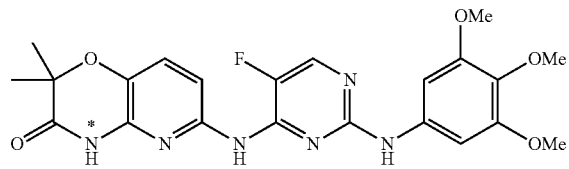

Compound 4

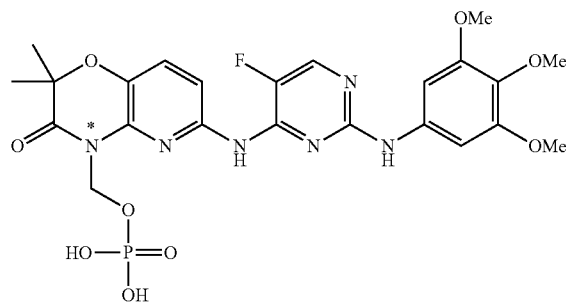

Significantly, whereas the water solubility of the active drug (Compound 1) is in the range of about 1-2 μg/ml in aqueous buffer under physiological conditions, the solubility of the corresponding phosphate prodrug (Compound 4) is greater than 5 mg/ml under the same conditions, or approximately 2000 times greater. This increased water-solubility allows for better dissolution in the gut, thereby facilitating oral administration. Other active 2,4-pyrimidinediamine compounds having similarly poor water solubilities are expected to exhibit similar increases in water solubility and oral bioavailability when formulated as phosphate prodrugs.

As mentioned above, phosphate ester prodrugs are generally less water-soluble than the corresponding phosphate prodrugs, and are therefore generally useful in applications where low water-solubility is desired, such as, for example, administration via inhalation. The same holds true for the relative water-solubility of phosphite ester and phosphite prodrugs.

In some embodiments, the prodrugs described herein are 2,4-pyrimidinediamine compounds that are substituted at the N4 nitrogen of the 2,4-pyrimidinediamine moiety with a substituted or unsubstituted nitrogen-containing bicyclic ring that includes at least one progroup $R^P$ as described herein at one or more of: the nitrogen atom(s) of the bicyclic ring, the N2 nitrogen of the 2,4-pyrimidinediamine moiety and/or the N4 nitrogen of the 2,4-pyrimidinediamine moiety. In a specific illustrative exemplary embodiment, the prodrug is a compound according to structural formula (I):

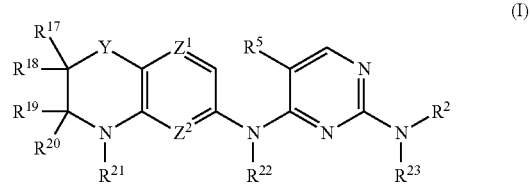

(I)

including salts, solvates, hydrates and N-oxides thereof, wherein:

Y is selected from $CH_2$, $NR^{24}$, O, S, S(O) and $S(O)_2$;

$Z^1$ and $Z^2$ are each, independently of one another, selected from CH and N;

$R^2$ is an optionally substituted lower alkyl, lower cycloalkyl, lower heteroalkyl, lower cycloheteroalkyl, aryl, phenyl, or heteroaryl group;

$R^5$ is an electronegative group, such as, for example, a halo, fluoro, cyano, nitro, trihalomethyl or trifluoromethyl group;

$R^{17}$ is selected from hydrogen, halogen, fluoro, lower alkyl and methyl or, alternatively, $R^{17}$ may be taken together with $R^{18}$ to form an oxo (=O) group or, together with the carbon atom to which they are attached, a spirocycle containing from 3 to 7 carbon atoms;

$R^{18}$ is selected from hydrogen, halogen, fluoro, lower alkyl and methyl or, alternatively, $R^{18}$ may be taken together with $R^{17}$ to form an oxo (=O) group or, together with the carbon atom to which they are attached, a spirocycle containing from 3 to 7 carbon atoms;

$R^{19}$ is selected from hydrogen, lower alkyl, and methyl or, alternatively, $R^{19}$ may be taken together with $R^{20}$ to form an oxo (=O) group or, together with the carbon atom to which they are attached, a spirocycle containing from 3 to 7 carbon atoms;

$R^{20}$ is selected from hydrogen, lower alkyl and methyl or, alternatively, $R^{20}$ may be taken together with $R^{19}$ to form an oxo (=O) group or, together with the carbon atom to which they are attached, a spirocycle containing from 3 to 7 carbon atoms;

$R^{21}$, $R^{22}$ and $R^{23}$ are each, independently of one another, selected from hydrogen and a progroup $R^P$ as described herein; and $R^{24}$ is selected from hydrogen, lower alkyl and a progroup $R^P$ as described herein, with the proviso that at least one of $R^{21}$, $R^{22}$, $R^{23}$ and $R^{24}$ must be a progroup $R^P$. In some embodiments, each of $R^{21}$, $R^{22}$ and $R^{23}$ is one of the specific progroups exemplified above and $R^{24}$ is hydrogen. In some embodiments $R^{21}$ is one of the specific progroups exemplified above and $R^{22}$, $R^{23}$ and $R^{24}$ are each hydrogen. In some embodiments, $R^{21}$, $R^{22}$ and $R^{23}$ are each one of the specific progroups exemplified above and $R^{24}$ is lower alkyl.

In another aspect, the present disclosure provides compositions comprising one or more of the prodrugs described herein and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

In still another aspect, the present disclosure provides intermediates useful for synthesizing the prodrugs described herein. In the case of phosphate- or phosphite-containing prodrugs, the intermediates generally comprise prodrugs in which the oxygen atoms of the phosphate- and/or phosphite-containing progroups are masked with protecting groups that are selectively removable under specified conditions. In some embodiments, the protecting groups are selectively removable under mildly acidic conditions. In some embodiments, the intermediates are phosphate or phosphite esters which are themselves prodrugs that can be metabolized into active 2,4-pyrimidinediamine compounds. In one illustrative embodiment, the intermediates include prodrugs in which each $R^P$ progroup is, independently of the others, of the formula —$(CR^dR^d)_y$—O—$P(O)(OR^i)(OR^i)$, —$(CR^dR^d)_y$—O—P(O)$(OR^i)(OH)$, —$(CR^dR^d)_y$—O—$P(OR^i)(OR^i)$ or —$(CR^dR^d)_y$—O—$P(OR^i)(OH)$, where each $R^i$ is, independently of the others, selected from lower unsubstituted alkanyl, substituted or unsubstituted phenyl and substituted or unsubstituted benzyl, and $R^d$ and y are as previously defined. In a specific embodiment, the intermediates include phosphate and/or phosphite esters in which each $R^i$ is, independently of the others, selected from lower linear alkanyl, lower branched alkanyl, i-propyl, t-butyl and lower cyclic alkanyl.

In some embodiments, the intermediates comprise an active 2,4-pyrimidinediamine that is substituted at a nitrogen atom of a primary or secondary amine group with a group of the formula —$CR^dR^d$—AH, where $R^d$ and A are as previously defined.

In yet another aspect, the present disclosure provides methods of synthesizing the intermediates and/or prodrugs described herein. Phosphate-containing prodrugs can be synthesized by reacting an active 2,4-pyrimidinediamine compound with a phosphate ester halide, for example, a phosphate ester halide of the formula X—$(CR^dR^d)_y$—O—$P(O)(OR^j)(OR^j)$ or X—$(CR^dR^d)_y$—O—$P(O)(OR^j)(OH)$, where each $R^j$ is, independently of the others, a selectively removable protecting group; X is a halide, such as, for example, chloride; and $R^d$ and y are as previously defined. In some embodiments, each $R^j$ is $R^e$, as previously defined. Removal of the selectively removable protecting groups $R^i$ yields a phosphate prodrug. In some embodiments each $R^j$ is the same and is selected from lower linear alkyl, lower branched alkyl and lower cycloalkyl. In some embodiments, each $R^j$ is isopropyl or t-butyl. In embodiments in which mixtures of intermediates are obtained, for example, mixtures of intermediates which contain different numbers of progroups or progroups at different positions on the 2,4-pyrimidinediamine molecule, the desired intermediate can be isolated from the mixture using standard separation and/or isolation techniques (e.g., column chromatography). Alternatively, a desired prodrug can be isolated from a mixture of different prodrugs using standard separation and/or isolation techniques.

Acyclic phosphate ester prodrugs can be obtained in an analogous manner by reacting the active 2,4-pyrimidinediamine with a phosphate ester halide, for example a phosphate ester halide of the formula X—$(CR^dR^d)_y$—O—$P(O)(OH)(OR^e)$ or X—$(CR^dR^d)_y$—O—$P(O)(OR^e)(OR^e)$, where X, $R^d$, y and $R^e$ are as previously defined. In this instance, removal of the esterifying groups $R^e$ is not necessary.

Acyclic phosphite and phosphite ester prodrugs can be prepared in an analogous manner from the corresponding phosphite ester halides, for example phosphite ester halides of the formula X—$(CR^dR^d)_y$—O—$P(OR^j)(OR^j)$, X—$(CR^dR^d)_y$—O—$P(OR^e)(OH)$, X—$(CR^dR^d)_y$—O—P$(OR^e)(OR^e)$, where X, $R^d$, y, $R^e$ and $R^j$ are as previously defined.

Cyclic phosphate ester and phosphite ester prodrugs can be prepared by reacting the active 2,4-pyrimidinediamine compound with the corresponding cyclic phosphate ester or phosphite ester halide, for example, a cyclic phosphate ester halide of the formula

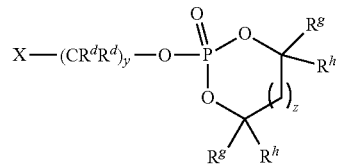

or a cyclic phosphite ester halide of the formula

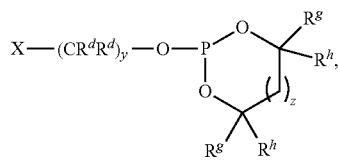

where X, $R^d$, y, z, $R^g$ and $R^h$ are as previously defined.

Embodiments in which $R^P$ is —$CR^dR^d$—$AR^3$ can be prepared from the corresponding 2,4-pyrimidinediamine drug using conventional methods. For example, when A is O, the intermediates can be synthesized by reacting an active 2,4-pyrimidinediamine compound, with an aldehyde or ketone of the formula $R^d$—C(O)—$R^d$, where $R^d$ is as previously defined, to yield a corresponding hydroxymethylamine intermediate (where $R^P$ is —$CR^dR^d$—OH). The hydroxymethylamine intermediate can then be converted into the prodrug using standard techniques. In accordance with the definition of $R^P$, the hydroxymethylamine intermediate is also a prodrug of the invention. For example, other drug substances containing secondary amines have been added to formaldehyde to afford their corresponding isolable hydroxymethylamine adducts, Bansal et al., *J. Pharmaceutical Sci.* 1981, 70: (8), 850-854; Bansal et al., *J. Pharmaceutical Sci.* 1981, 70: (8), 855-856; Khan et al., *J. Pharmaceutical and Biomedical Analysis* 1989, 7 (6), 685-691. Alternatively, hydroxyalkyl-containing prodrugs can be prepared in two steps by first reacting the active 2,4-pyrimidinediamine with a bis-functional electrophile, such as a halide of the formula $X^1$—$CR^dR^d$—$X^2$, where $X^1$ represents a first halide, $X^2$ represents a second halide and $R^d$ is as previously defined. In a specific exemplary embodiment, the halide is of the formula I—$CR^dR^d$—Cl. The unreacted halide is then hydroxylated to yield the hydroxyalkyl-containing prodrug using standard techniques.

Prodrugs in which A is O, S or $NR^{50}$ can be synthesized from corresponding N-methyl phosphate esters. According to this embodiment, the phosphate ester groups can be displaced with a group of the formula $R^3$—AH, where $R^3$ and A are as previously defined, to yield the prodrug, as discussed in further detail below.

In the prodrugs described herein, and in particular in the prodrugs of structural formula (I), $R^{21}$, $R^{22}$ and $R^{23}$ each represent either hydrogen or a progroup $R^P$. Also, $R^{24}$ represents hydrogen, a lower alkyl or a progroup $R^P$. Thus, the prodrugs can include a single $R^P$ progroup, two $R^P$ progroups, three $R^P$ progroups, or even more $R^P$ progroups, depending, in part, on the identity of Y and whether the $R^2$ substituent includes any $R^P$ progroups. In some embodiments, it is preferred that the prodrugs described herein, and in particular the prodrugs of structural formula (I), include only one $R^P$ group. Without intending to be bound by any theory of operation, it is possible that the different $R^P$ groups in prodrugs including more than one $R^P$ progroup may metabolize at different rates. Prodrugs including a single $R^P$ progroup would avoid such differential metabolic kinetics. A specific embodiment of prodrugs according to structural formula (I) that include a single progroup $R^P$ are compounds according to structural formula (Ia):

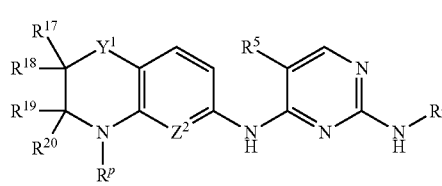
(Ia)

wherein $Y^1$ is selected from $CH_2$, $NR^{24}$, O, S, S(O) and $S(O)_2$; and $Z^2$, $R^2$, $R^5$, $R^{17}$, $R^{18}$, $R^{19}$, $R^{20}$, $R^{24}$ and $R^P$ are as previously defined, with the proviso that $R^2$ does not include any $R^P$ groups.

The identity of any $R^P$ progroups present in the prodrugs described herein is not critical for success, provided that it hydrolyzes under the conditions of use to yield the active 2,4-pyrimidinediamine compound. It has recently been discovered that a phosphate-containing prodrug according to the structure illustrated below:

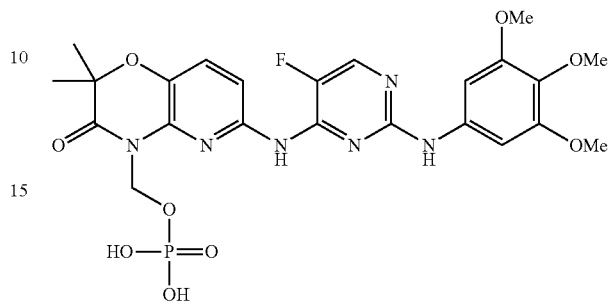

metabolizes in vivo to the corresponding active 2,4-pyrimidinediamine compound (Compound 1), illustrated below:

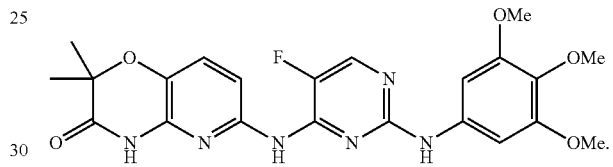

While not intending to be bound by any particular theory operation, it is believed that this prodrug metabolizes to active Compound 1 via the corresponding hydroxymethylamine intermediate illustrated below:

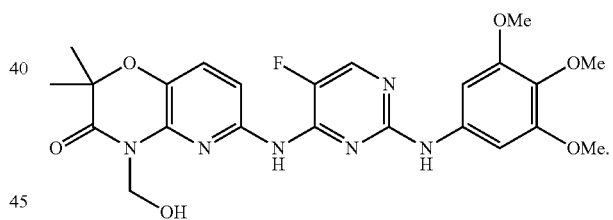

Such hydroxymethylamine compound are known to be unstable under physiological conditions and various pH ranges where they hydrolyze in vivo to yield formaldehyde and the active drug substance. Based on this observation, it is believed that prodrugs that include hydroxyl "protecting" groups that can be metabolized in vivo, for example by the acidic conditions of the stomach and/or by enzymes present in the digestive tract or other organs and/or tissues or fluids with the body, to yield the hydroxymethylamine intermediate illustrated above will likewise metabolize to the active 2,4 pyrimidinediamine drug.

Moreover, it is expected that the amino and thio analogs of this hydroxymethylamine intermediate, will be similarly unstable at physiological conditions and also hydrolyze in vivo to the active 2,4-pyrimdiendiamine drug. Accordingly, it is also expected that the corresponding amino and thio compounds, as well as compounds in which the α-amino and α-thio groups are masked with "protecting" groups that are removed under physiological conditions of use to yield the α-amino and α-thio groups, will likewise make suitable prodrugs.

Thus, in some embodiments, the progroup(s) $R^P$ in the prodrugs of structural formulae (I) and (Ia) are of the formula —$CR^dR^d$—A—$R^3$, where each $R^d$ is, independently of the other, selected from hydrogen, cyano, —C(O)$R^e$, —C(O)O$R^e$, —C(O)NR$^e$R$^e$, —C(OR$^e$)(OR$^e$), optionally substituted (C1-C20) alkyl, (C1-C20) perfluoroalkyl, optionally substituted (C7-C30) arylalkyl and optionally substituted 6-30 membered heteroarylalkyl, where each $R^e$ is, independently of the others, selected from hydrogen, alkyl (for example lower alkyl), aryl (for example phenyl or naphthyl, arylalkyl (for example benzyl), heteroaryl and heteroarylalkyl; A is selected from O, S and NR$^{50}$, where $R^{50}$ is selected from $R^d$ and cycloalkyl, or, alternatively, is taken together with $R^3$ such that $R^{50}$ and $R^3$, together with nitrogen atom to which they are attached, form a three- to seven-membered ring; and $R^3$ is a group that, together with A, metabolizes under the conditions of use to yield an intermediate group of the formula —$CR^dR^d$AH, where $R^d$ and A are as previously defined. As mentioned above, compounds of structural formula (I) and (Ia) in which the $R^P$ groups are of the formula —$CR^dR^d$—AH spontaneously hydrolyze in vivo to yield the active 2,4-pyrimidinediamine drug.

The mechanism by which the $R^3$ group metabolizes to yield intermediate group —$CR^dR^d$—A—H is not critical, and can be caused by, for example, hydrolysis under the acidic conditions of the stomach, and/or by enzymes present in the digestive tract and/or tissues or organs of the body. Indeed, the $R^3$ group(s) can be selected to metabolize at a particular site within the body. For example, many esters are cleaved under the acidic conditions found in the stomach. Prodrugs designed to cleave chemically in the stomach to the active 2,4-pyrimidinediamine can employ progroups including such esters. Alternatively, the progroups may be designed to metabolize in the presence of enzymes such as esterases, amidases, lipolases, phosphatases including ATPases and kinase etc., to yield the intermediate group of formula —$CR^dR^d$—A—H. Progroups including linkages capable of metabolizing in vivo to yield such an intermediate group are well-known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

The identity of the $R^3$ group can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The $R^3$ group can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al., 2004, J. Med. Chem. 47(10:2393-2404), the disclosure of which is incorporated by reference. All of the various groups described in these references can be utilized in the prodrugs described herein.

In some embodiments, $R^3$ is selected from —$R^f$, —C(O) $R^f$, —C(O)NR$^f$R$^f$ and —SIR$^f$R$^f$R$^f$, where the $R^f$ groups are selected so as to impart the prodrugs with desired bioavailability, cleavage and/or targeting properties. In a specific embodiment, the $R^f$ groups are selected to impart the prodrug with higher water-solubility than the underlying active 2,4-pyrimidinediamine drug. Thus, in some embodiments, the $R^f$ groups are selected such that they, taken together with the heteroatom or group to which they are bonded, are hydrophilic in character. Such hydrophilic groups can be charged or uncharged, as is well-known in the art. As specific examples, the $R^f$ groups may be selected from hydrogen, optionally substituted lower alkyl, optionally substituted lower heteroalkyl, optionally substituted lower cycloalkyl, optionally substituted lower heterocycloalkyl, optionally substituted (C6-C10) aryl, optionally substituted 5-10 membered heteroaryl, optionally substituted (C7-C18) arylalkyl and optionally substituted 6-18 membered heteroarylalkyl. The nature of any present substituents can vary widely, as is known in the art. In some embodiments any present substituents are, independently of one another, selected from $R^h$, defined above.

In a specific embodiment, the progroups on the prodrugs of formula (I) and/or (Ia) are of the formula —$CR^dR^d$—A—$R^3$, where $R^3$ is selected from —(CH$_2$)$_i$—$R^b$, —C(O)$R^a$, —C(O)—(CH$_2$)$_i$—$R^b$, —C(O)O—$R^a$ and —C(O)O—(CH$_2$)$_i$—$R^b$, where X, $R^a$, $R^b$ and $R^d$ are as previously defined, and i is an integer ranging from 0 to 6. Specific, non-limiting, examples of exemplary water-solubility increasing progroups include by the way of example and not limitation, hydrophilic groups such as alkyl, arylk, arylalkyl, or cycloheteroalkyl groups substituted with one or more of an amine, alcohol, a carboxylic acid, a phosphorous acid, a sulfoxide, a sugar, an amino acid, a thiol, a polyol, a ether, a thioether and a quaternary amine salt.

One important class of progroups includes progroups that contain a phosphate group, for example, phosphate-containing progroups of the formula —($R^dR^d$)$_y$—O—P(O)(OH)$_2$, where $R^d$ is as defined above and y is an integer ranging from 1 to 3, typically 1 or 2. In a specific embodiment, each $R^d$ is, independently of the others, selected from hydrogen, substituted or unsubstituted lower alkyl, substituted or unsubstituted (C6-C14) aryl and substituted or unsubstituted (C7-C20) arylalkyl.

While not intending to be bound by any theory of operation, it is believed that such phosphate-containing progroups $R^P$ act as substrates for both alkaline and acid phosphatase enzymes, leading to their removal from the prodrugs under physiological conditions of use. As alkaline phosphatases are abundant in the digestive tract of humans, phosphate-containing progroups $R^P$ that can be cleaved in the presence of alkaline phosphatases are particularly suitable for formulating phosphate-containing prodrugs intended for oral administration. Specific examples of phosphate-containing progroups $R^P$ suitable for use in prodrugs intended for oral administration include, but are not limited to, groups of the formula —($R^dR^d$)$_y$—O—P(O)(OH)$_2$ in which each $R^d$ is, independently of the others, selected from hydrogen and unsubstituted lower alkanyl. Exemplary embodiments of such phosphate-containing progroups include, but are not limited to,—CH$_2$—O—P(O)(OH)$_2$ and —CH$_2$CH$_2$—O—P(O)(OH)$_2$.

In some embodiments of such prodrugs, the phosphorous-containing progroup $R^P$ comprises a phosphite group. A specific exemplary embodiment of such phosphite-containing progroups includes prodrug compounds in which the progroup $R^P$ is of the formula —($CR^dR^d$)$_y$—O—P(OH)(OH), where $R^d$ and y are as previously defined.

In other embodiments of such prodrugs, the phosphorous-containing progroup $R^P$ comprises an acyclic phosphate ester or phosphite ester group. Specific exemplary embodiments of such acyclic phosphate ester and phosphite ester prodrugs include progroups $R^P$ of the formula —$(CR^dR^d)_y$—O—P(O)(OH)(OR$^e$), —$(CR^dR^d)_y$—O—P(O)(OR$^e$)$_2$, —$(CR^dR^d)_y$—O—P(OH)(OR$^e$) and —$(CR^dR^d)_y$—O—P(OR$^e$)$_2$, where R$^e$ is selected from substituted or unsubstituted lower alkyl, substituted or unsubstituted (C6-C14) aryl (e.g., phenyl, naphthyl, 4-lower alkoxyphenyl, 4-methoxyphenyl), substituted or unsubstituted (C7-C20) arylalkyl (e.g., benzyl, 1-phenylethan-1-yl, 2-phenylethan-1-yl), —$(CR^dR^d)_y$—OR$^f$, —$(CR^dR^d)_y$—O—C(O)R$^f$, —$(CR^dR^d)_y$—O—C(O)OR$^f$, —$(CR^dR^d)_y$—S—C(O)R$^f$, —$(CR^dR^d)_y$—S—C(O)OR$^f$, —$(CR^dR^d)_y$—NH—C(O)R$^f$, —$(CR^dR^d)_y$—NH—C(O)OR$^f$ and —Si(R$^d$)$_3$, wherein each R$^f$ is, independently of the others, selected from hydrogen, unsubstituted or substituted lower alkyl, substituted or unsubstituted (C6-C14) aryl, and substituted or unsubstituted (C7-C20) arylalkyl, and R$^d$ and y are as previously defined.

In still other embodiments, phosphorous-containing prodrugs that include phosphate precursors are prodrugs in which the phosphorous-containing progroup R$^P$ comprises a cyclic phosphate ester of the formula

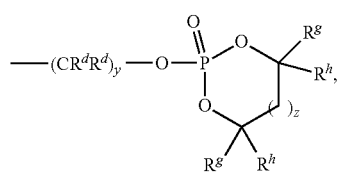

where each R$^g$ is, independently of the others, selected from hydrogen and lower alkyl; each R$^h$ is, independently of the others, selected from hydrogen, substituted or unsubstituted lower alkyl, substituted or unsubstituted lower cycloheteroalkyl, substituted or unsubstituted (C6-C14) aryl, substituted or unsubstituted (C7-C20) arylalkyl and substituted or unsubstituted 5-14 membered heteroaryl; z is an integer ranging from 0 to 2; and R$^d$ and y are as previously defined.

In still other embodiments, phosphorous-containing prodrugs that include phosphate precursors are prodrugs in which the phosphorous-containing progroup R$^P$ comprises a cyclic phosphite ester of the formula

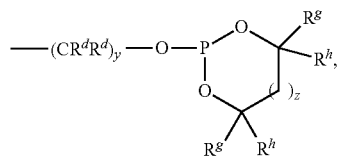

where R$^g$, R$^h$, R$^d$, y and z are as previously defined.

In some embodiments, the substituents R$^h$ on such cyclic phosphate ester and phosphite ester prodrugs are selected such that the progroup is metabolized in vitro by esterase enzymes. Specific examples of such phosphate ester and phosphite ester progroups include those in which each R$^h$ is, independently of the others, selected from hydrogen, lower alkyl, methyl, ethyl and propyl. In some embodiments, such progroups are selected from

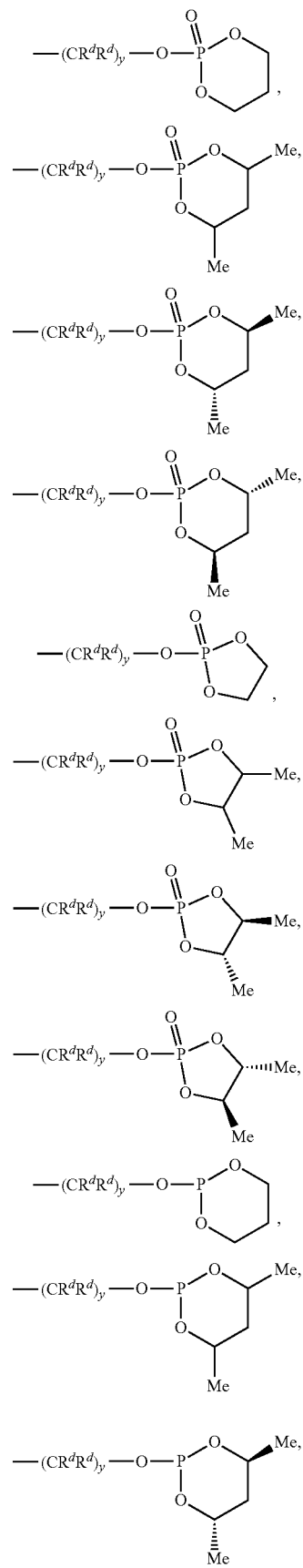

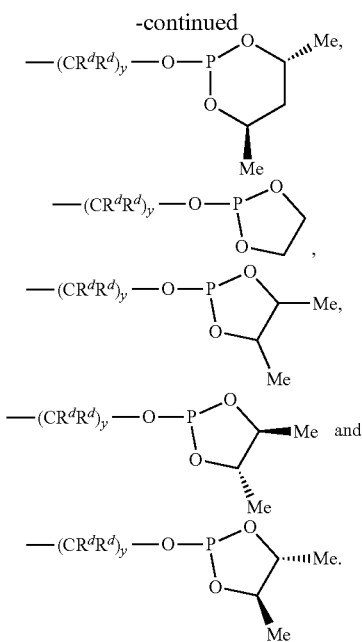

Many of these phosphate esters and phosphite esters are acid label and, when administered orally, metabolize to the corresponding phosphates and phosphites under the acidic conditions of the stomach and/or gut.

Thus, in the phosphorous-containing prodrugs described herein, the identity of the particular phosphorous-containing progroups $R^P$ employed can be selected to tailor the prodrugs for particular modes of delivery, etc.

The suitability of any particular progroup $R^P$ for a desired mode of administration can be confirmed in biochemical assays. For example, if a prodrug is to be administered by injection into a particular tissue or organ, and the identities of the various phosphatases expressed in the tissue or organ are known, the particular prodrug can be tested for metabolism in biochemical assays with the isolated phosphatase(s). Alternatively, the particular prodrug can be tested for metabolism to the active 2,4-pyrimidinediamine compound with tissue and/or organ extracts. Using tissue and/or organ extracts can be of particular convenience when the identity(ies) of the phosphatases expressed in the target tissues or organs are unknown, or in instances when the isolated phosphatases are not conveniently available. Skilled artisans will be able to readily select progroups $R^P$ having metabolic properties (such as kinetics) suitable for particular applications using such in vitro tests. Of course, specific prodrugs could also be tested for suitable metabolism in in vitro animal models.

In some embodiments, the prodrugs are prodrugs according to structural formula (I) or (Ia) that have one or more features selected from:
(i) $R^5$ is fluoro;
(ii) $R^2$ is a phenyl optionally substituted with one or more of the same or different $R^8$ groups;
(iii) $R^2$ is 3,4,5-tri(loweralkoxy)phenyl;
(iv) $R^2$ is 3,4,5-trimethoxyphenyl;
(v) Y or $Y^1$ is O; $Z^1$ is CH, $Z^2$ is N; $R^{17}$ and $R^{18}$ are each methyl; and $R^{19}$ and $R^{20}$ are taken together to form an oxogroup; and
(vi) $R^P$ is a hydroxyalkyl-containing progroup of the formula —$CH_2OH$, or a phosphate-containing progroup of the formula —$(CR^dR^d)_y$—O—P(O)(OH)$_2$, or a phosphate ester, phosphite or phosphite ester analog thereof, wherein y is 1 or 2 and each $R^d$ is, independently of the others, selected from hydrogen and unsubstituted lower alkyl, or
(vii) $R^P$ is selected from —$CH_2OH$, $CH_2$—SH, —$CH_2$—$NH_2$, —$CH_2$—$NHR^{50}$, —$CH_2$—$N(R^{50})_2$, —$CH_2$—A—$R^f$, —$CH_2$—A—$C(O)R^f$, —$CH_2$—A—$C(O)OR^f$ and —$CH_2$—A—$C(O)NR^fR^f$, where A, $R^{50}$ and $R^f$ are as previously defined.

In some embodiments, the prodrugs of structural formulae (I) and (Ia) have two or three of the above-delineated features. In one specific embodiment, the prodrugs have features (i), (iii) and (v). In another specific embodiment, the prodrugs have features (i), (iv) and (v). In still another specific embodiment, the prodrugs have features (i), (iii), (v) and (vi) or (vii). In still another specific embodiment, the prodrugs have features (i), (iv), (v) and (vi) or (vii). In still another specific embodiment, $R^P$ is a phosphate-containing progroup of the formula —$(CR^dR^d)_y$—O—P(O)(OH)$_2$.

In all of the compounds described herein that include substituent alternatives that may be substituted, such as, for example, some of the substituent alternatives delineated for $R^d$, $R^e$, $R^f$, $R^g$, $R^h$, $R^i$ and $R^j$, the substitutions are typically, independently of one another, selected from amongst the $R^b$ groups described in connection with structural formula (I). In a specific embodiment, any present substitutions are, independently of one another, selected from hydroxyl, lower alkoxy, (C6-C14) aryloxy, lower alkoxyalkyl, methoxymethyl, methoxyethyl, ethoxymethyl, ethoxyethyl and halogen.

Those of skill in the art will appreciate that many of the prodrugs described herein, as well as the various prodrug species specifically described and/or illustrated herein, may exhibit the phenomena of tautomerism, conformational isomerism, geometric isomerism and/or optical isomerism. For example, the prodrugs may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the prodrugs may exist in several tautomeric forms, including the enol form, the keto form and mixtures thereof. As the various compound names, formulae and drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the prodrugs having one or more of the utilities described herein, as well as mixtures of these various different isomeric forms. In cases of limited rotation around the 2,4-pryimidinediamine moiety, atrop isomers are also possible and are also specifically included in the compounds of the invention.

Moreover, skilled artisans will appreciate that when lists of alternative substituents include members which, owing to valency requirements or other reasons, cannot be used to substitute a particular group, the list is intended to be read in context to include those members of the list that are suitable for substituting the particular group. For example, skilled artisans will appreciate that while all of the listed alternatives for $R^b$ can be used to substitute an alkyl group, certain of the alternatives, such as =O, cannot be used to substitute a phenyl group. It is to be understood that only possible combinations of substituent-group pairs are intended.

The prodrugs described herein may be identified by either their chemical structure or their chemical name. When the chemical structure and the chemical name conflict, the chemical structure is determinative of the identity of the specific prodrug.

Depending upon the nature of the various substituents, the prodrugs described herein may be in the form of salts. Such salts include salts suitable for pharmaceutical uses ("pharmaceutically-acceptable salts"), salts suitable for veterinary uses, etc. Such salts may be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The prodrugs described herein, as well as the salts thereof, may also be in the form of hydrates, solvates and N-oxides, as are well-known in the art. Unless specifically indicated otherwise, the expression "prodrug" is intended to encompass such salts, hydrates, solvates and/or N-oxides. Specific exemplary salts include, but are not limited to, mono- and di-sodium salts, mono- and di-potassium salts, mono- and di-lithium salts, mono- and di-alkylamino salts, mono-magnesium salts, mono-calcium salts and ammonium salts.

Additional aspects of prodrugs suitable for the invention are described in U.S. Pat. No. 7,449,458, the disclosure of which is incorporated herein by reference.

Pharmaceutical Compositions

In certain embodiments, he present disclosure provides pharmaceutical compositions that include a pharmaceutically acceptable carrier and a therapeutically effective amount of a compound or prodrug of the present disclosure or a pharmaceutically acceptable salt or solvate or stereoisomer thereof.

A pharmaceutical composition that includes a subject compound may be administered to a patient alone, or in combination with other supplementary active agents. For example, one or more compounds according to the present disclosure can be administered to a patient with or without supplementary active agents. The pharmaceutical compositions may be manufactured using any of a variety of processes, including, but not limited to, conventional mixing, dissolving, granulating, dragee-making, levigating, emulsifying, encapsulating, entrapping, lyophilizing, and the like. The pharmaceutical composition can take any of a variety of forms including, but not limited to, a sterile solution, suspension, emulsion, spray dried dispersion, lyophilisate, tablet, microtablets, pill, pellet, capsule, powder, syrup, elixir or any other dosage form suitable for administration.

A subject compound or prodrug may be administered to a subject using any convenient means capable of resulting in the desired reduction in disease condition or symptom. Thus, a subject compound or prodrug can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, aerosols, and the like.

In certain embodiments, a subject compound or prodrug may be formulated as a pharmaceutical composition, where the pharmaceutical composition is an oral dosage formulation, such as a tablet. Additional aspects of oral dosage formulations (e.g., tablets) suitable for the invention are described in U.S. Pat. No. 8,771,648, the disclosure of which is incorporated herein by reference.

Formulations for pharmaceutical compositions are described in, for example, Remington's Pharmaceutical Sciences, by E. W. Martin, Mack Publishing Co., Easton, Pa., 19th Edition, 1995, which describes examples of formulations (and components thereof) suitable for pharmaceutical delivery of disclosed compounds or prodrugs. Pharmaceutical compositions that include at least one of the subject compounds or prodrugs can be formulated for use in human or veterinary medicine. Particular formulations of a disclosed pharmaceutical composition may depend, for example, on the mode of administration and/or on the location of the subject to be treated. In some embodiments, formulations include a pharmaceutically acceptable carrier in addition to at least one active ingredient, such as a subject compound or prodrug. In other embodiments, other medicinal or pharmaceutical agents, for example, with similar, related or complementary effects on the disease or condition being treated can also be included as active ingredients in a pharmaceutical composition.

Pharmaceutically acceptable carriers useful for the disclosed methods and compositions may depend on the particular mode of administration being employed. For example, parenteral formulations may include injectable fluids, such as, but not limited to, pharmaceutically and physiologically acceptable fluids such as water, physiological saline, balanced salt solutions, aqueous dextrose, glycerol or the like as a vehicle. For solid compositions (e.g., powder, pill, tablet, or capsule forms), non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other examples of excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) water (e.g., pyrogen-free water); (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound or prodrug. Examples of pharmaceutically acceptable salts include non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, methyl sulfonic acid, salicylic acid, formic acid, trichloroacetic acid, trifluoroacetic acid, gluconic acid, asparagic acid, aspartic acid, benzenesulfonic acid, para-toluenesulfonic acid, naphthalenesulfonic acid, combinations thereof, and the like. In certain embodiments, the pharmaceutically acceptable salt includes formic acid. Other examples of pharmaceutically acceptable salts include non-toxic salts of a free acid form of compounds or prodrugs according to the present disclosure. Such salts are derived from inorganic or organic bases. Pharmaceutically acceptable base addition salts include those derived from inorganic bases such as sodium, potassium, lithium, ammonium, calcium, magnesium, iron, zinc, copper, manganese, aluminum salts, combinations thereof, and the like. Examples of salts are the ammonium, potassium, sodium, calcium, and magnesium salts. Salts of the presently disclosed compounds or prodrugs can be derived from pharmaceutically acceptable organic non-toxic bases including, but not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, 2-amino-2-hydroxymethyl-propane-1,3-diol ("Tris" salt), dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, combinations thereof, and the like. Pharmaceutically acceptable salts are described further in S. M. Berge, et al., "Pharmaceutical Salts," J. Pharm. Sci., 1977; 66:1-19 and Remington's Pharmaceutical Sciences, 19th Edition, Mack Publishing Company, Easton, Pa., 1995.

In certain embodiments, a subject compound or prodrug is formulated as a pharmaceutically acceptable salt, where the pharmaceutically acceptable salt is a disodium hexahydrate form of the subject compound or prodrug. Additional aspects of salts and hydrates of the subject compounds and prodrugs suitable for the invention are described in U.S. Pat. No. 8,163,902 and U.S. Pat. No. 8,445,485, the disclosures of which are incorporated herein by reference.

A subject compound or prodrug can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound or prodrug can be formulated into preparations for injection by dissolving, suspending or emulsifying the compound in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

A subject compound or prodrug can be utilized in aerosol formulation to be administered intrapulmonarily (e.g., via inhalation). A subject compound or prodrug can be formulated into pressurized acceptable propellants such as dichlorodifluoromethane, propane, nitrogen and the like.

Furthermore, a subject compound or prodrug can be made into suppositories by mixing with a variety of bases such as emulsifying bases or water-soluble bases. A subject compound or prodrug can be administered rectally via a suppository. The suppository can include vehicles such as cocoa butter, carbowaxes and polyethylene glycols, which melt at body temperature, yet are substantially solid at room temperature.

The term "unit dosage form," as used herein, refers to physically discrete units suitable as unitary dosages for human and animal subjects, each unit containing a predetermined quantity of a subject compound or prodrug calculated in an amount sufficient to produce the desired effect in association with a pharmaceutically acceptable diluent, carrier or vehicle. The specifications for a subject compound or prodrug depend on the particular compound employed and the effect to be achieved, and the pharmacodynamics associated with each compound or prodrug in the host.

The dosage form of a disclosed pharmaceutical composition may be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). In other embodiments, the subject compounds or prodrugs may be formulated for intrapulmonary administration. For example, intrapulmonary formulations of the subject prodrugs may include, but are not limited to, dry powder or solution formulations, and intrapulmonary formulations of the subject compounds may include, but are not limited to, dry powder or suspension formulations. Methods of preparing such dosage forms are known, or will be apparent, to those skilled in the art.

Certain embodiments of the pharmaceutical compositions that include a subject compound or prodrug may be formulated in unit dosage form suitable for individual administration of precise dosages. The amount of active ingredient administered may depend on the subject being treated, the severity of the affliction, and the manner of administration, and is known to those skilled in the art. In certain instances, the formulation to be administered contains a quantity of the compounds or prodrugs disclosed herein in an amount effective to achieve the desired effect in the subject being treated.

Each therapeutic compound or prodrug can independently be in any dosage form, such as those described herein, and can also be administered in various ways, as described herein. For example, the compounds or prodrugs may be formulated together, in a single dosage unit (that is, combined together in one form such as capsule, tablet, powder, or liquid, etc.) as a combination product. Alternatively, when not formulated together in a single dosage unit, an individual subject compound or prodrug may be administered at the same time as another therapeutic compound or prodrug or sequentially, in any order thereof.

A disclosed compound or prodrug can be administered alone, as the sole active pharmaceutical agent, or in combination with one or more additional compounds or prodrugs of the present disclosure or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of the present disclosure optionally include other therapeutic agents. Accordingly, certain embodiments are directed to such pharmaceutical compositions, where the composition further includes a therapeutically effective amount of an agent selected as is known to those of skill in the art.

Combination Therapy

The present compound may be is administered in combination with one or more other therapeutic agents, the other therapeutic agents may target SARS-CoV-2 or any of the symptoms of COVID-19 infection. The agents include (a) inhibitors of cell entry of SARS-CoV-2, (b) inhibitors of replication, membrane fusion and assembly of SARS-CoV-2 and (c) phytochemicals and natural products that target coronaviruses. The present therapy may be combined with plasma therapy in some cases.

Inhibitors of Cell Entry of SARS-CoV-2

Inhibitors of cell entry of SARS-CoV-2 include inhibitors of TMPRSS2 serine protease and inhibitors of angiotensin-converting enzyme 2 (ACE2).

Inhibitors of TMPRSS2 serine protease include, but are not limited to:

Camostat Mesilate (Foipan™)
Camostat, (FOY-305), [N,N-dimethylcarbamoylmethyl 4-(4-guanidinobenzoyloxy)-phenylacetate]methanesulfate and camostat mesilate (Foipan™), alternatively termed camostat mesylate, (NI-03), (CAS number: 59721-28-7).

Nafamostat Mesilate (Buipel™)
Nafamostat mesilate (Buipel™), (6-amidino-2-naphthyl-4-guanidino benzoate-dimethanesulfonate) (FUT-175), (CAS number: 81525-10-2).

Inhibitors of ACE2 and antimalarial/parasiticide drugs include, but are not limited to:

Chloroquine Phosphate and Hydroxychloroquine
Chloroquine phosphate (Resochin™) and its derivative hydroxychloroquine (Quensyl™, Plaquenil™, Hydroquin™, Dolquine™, Quinoric™), which have been used for decades for the prophylaxis and treatment of malaria have recently been demonstrated as potential broad-spectrum antiviral drugs.

Cepharanthine/Selamectin/Mefloquine Hydrochloride
The triple combination of cepharanthine (an anti-inflammatory alkaloid from *Stephania cepharantha* Hayata), (CAS number: 48,104,902), selamectin (an avermectin isolated from *Streptomyces avermitilis* and used as an anti-helminthic and parasiticide drug in veterinary medicine), (CAS number. 220119-17-5), and mefloquine hydrochloride (Lariam™, used for the prophylaxis and treatment of malaria) has been shown to inhibit infection of simian Vero E6 cells with pangolin coronavirus GX_P2V/2017/Guangxi (GX_P2V).

Experimental Inhibitors of ACE2

In addition to the above, there are a number of experimental inhibitors of ACE2, including peptide inhibitors (e.g., DX600, which had a $K_i$ of 2.8 nm and an $IC_{50}$ of 10.1 μM (Huang et al, J. Biol. Chem. 2003; 278:15532-15540), di-peptide and tripeptides), small-molecules (e.g., MLN-4760 (CAS number: 305335-31-3), N-(2-aminoethyl)-1 aziridine-ethanamine and the TNF-α converting enzyme (TACE) small-molecule inhibitor TAPI-2). In addition, the phytochemical nicotianamine (CAS number: 34441-14-0), a metal chelator ubiquitously present in higher plants may be used since it is a potent inhibitor of human ACE2 with an $IC_{50}$ of 84 nM.

Casirivimab (REGN10933)

Casirivimab is a monoclonal antibody designed specifically to block infectivity of SARS-CoV-2. Casirivmab was permitted Emergency Use Authorization (EUA) by the FDA to be used in combination with imdevimab. The two potent, virus-neutralizing antibodies that form the cocktail bind non-competitively to the critical receptor binding domain of the virus's spike protein, which diminishes the ability of mutant viruses to escape treatment and protects against spike variants that have arisen in the human population.

Imdevimab (REGEN10987)

Imdevimab is a monoclonal antibody designed specifically to block infectivity of SARS-CoV-2. Imdevimab was permitted EUA by the FDA to be used in combination with Casirivimab. The two potent, virus-neutralizing antibodies that form the cocktail bind non-competitively to the critical receptor binding domain of the virus's spike protein, which diminishes the ability of mutant viruses to escape treatment and protects against spike variants that have arisen in the human population.

Casirivimab and imdevimab may be administered together, e.g., separately or as a mixture. This combination is also known as the Regeneron antibody cocktail.

Bamlanivimab (LY-CoV555)

Bamlanivimab is a recombinant neutralizing human IgG1k monoclonal antibody that binds to the receptor-binding domain of the spike protein of SARS-CoV-2 and prevents the attachment of spike protein with the human ACE2 receptor. Bamlanivimab has been permitted EUA by the FDA to be used in conjunction with etesevimab in patients with mild to moderate symptoms of COVID-19 in non-hospitalized adults and adolescents, and who are at high risk for developing severe COVID-19 symptoms or the need for hospitalization.

Etesevimab (LY-CoV016)

Etesevimab (LY-CoV016, also known as JS016) is a recombinant fully human monoclonal neutralizing antibody, which specifically binds to the SARS-CoV-2 surface spike protein receptor binding domain with high affinity and can block the binding of the virus to the ACE2 host cell surface receptor. Etesevimab has been permitted EUA by the FDA to be used in conjunction with Bamlanivimab in patients with mild to moderate symptoms of COVID-19 in non-hospitalized adults and adolescents, and who are at high risk for developing severe COVID-19 symptoms or the need for hospitalization.

Bamlanivimab and etesevimab may be administered together, e.g., separately or as a mixture. This combination is also known as the Lilly antibody cocktail Inhibitors of Replication, Membrane Fusion and Assembly of SARS-CoV-2

These agents include ribonucleoside analogs, protease inhibitors, inhibitors of membrane fusion, guanine analogs and other compounds, examples of which are described below.

Remdesivir (VeKlury)

Remdesivir (GS-5734), (CAS number: 1809249-37-3), is a small-molecule adenine nucleotide analogue antiviral drug that has shown efficacy against Ebola virus in rhesus monkeys. This agent can be administered daily by intravenous administration of 10 mg kg (−1) remdesivir for several days. Remdesivir is a prodrug that is metabolized into its active form GS-441524, an adenine nucleotide analogue that interferes with the activity of viral RNA-dependent RNA polymerase (RdRp) and that promotes evasion of proofreading by viral exoribonuclease, leading to inhibition of viral RNA synthesis. This agent prophylactic and therapeutic activity. Remdesivir has been approved by the FDA for the treatment of COVID-19 requiring hospitalization.

$N^4$-Hydroxyctidine

N4-Hydroxyctidine, or EIDD-1931, is a ribonucleoside analog which induces mutations in RNA virions. N4-hydroxycytidine N4-hydroxycytodine has been shown to inhibit SARS-CoV-2 as well as other human and bat coronaviruses in mice and human airway epithelial cells. Sheahan et al. Sci. Transl. Med. 2020 12 541. N4-hydroxycytidine or a prodrug (e.g., EIDD-2801) can be used. The prodrug of N4-hydroxycytidine, EIDD-2801, is also being investigated for its broad spectrum activity against the coronavirus family of viruses.3

Lopinavir/Ritonavir (Kaletra™)

Lopinavir (ABT-378) is a highly potent inhibitor of the human immunodeficiency virus (HIV) protease essential for intracellular HIV assembly The combination of lopinavir and ritonavir (Kaletra™) has been established as an effective oral drug for the treatment of patients infected by coronavirus. Patients can be treated with the combination of lopinavir (400mg)/ritonavir (100 mg) orally every 12 h for 14 days, for example.

Umifenovir (Arbidol™)

Umifenovir (Arbidol™), (ethyl-6-bromo-4-[(dimethylamino)methyl]-5-hydroxy-1-methyl-2[(phenylthio)methyl]-indole-3-carboxylate hydrochloride monohydrate), (CAS number: 131707-25-0), is a small indole-derivate molecule that prevents viral host cell entry by inhibition of membrane fusion of viral envelope and host cell cytoplasmic membrane via inhibition of clathrin-mediated endocytosis.

Favipiravir (Avigan™)

Favipiravir (Avigan™), (T-705), (6-fluoro-3-hydroxy-2-pyrazinecarboxamide), (CAS number: 259793-96-9), is an oral pyrazinecarboxamide derivative and guanine analogue that selectively and potently inhibits the RNA-dependent RNA polymerase (RdRp) of RNA viruses and induces lethal RNA transversion mutations, thereby producing a nonviable virus phenotype. Favipiravir inhibits replication of a large number of RNA viruses, including influenza A virus, flavi-, alpha-, filo-, bunya-, arena- and noroviruses as well as West Nile virus, yellow fever virus, foot-and-mouth-disease virus, Ebola virus and Lassa virus.

This treatment may be combined with a monoclonal antibody against the human interleukin-6 receptor, tocilizumab, or chloroquine phosphate for example.

Inhibitors of SARS-CoV-2 3Clpro Protease

3Clpro (also termed Mpro) constitutes the main protease of beta coronaviruses that is essential for processing of polyproteins translated from the viral RNA. An inhibitor of 3Clpro, termed N3, has been identified by computer-aided drug design. N3, a Michael acceptor inhibitor that can inhibit the 3Clpros of SARS-CoV and MERS-CoV can also be used.

Oseltamivir (Tamiflu)

Oseltamivir (GS-4104) is a neuraminidase inhibitor, a competitive inhibitor of influenza's neuraminidase enzyme. The enzyme cleaves the sialic acid which is found on glycoproteins on the surface of human cells that helps new virions to exit the cell. Thus oseltamivir prevents new viral particles from being released.

Immunomodulators

Dexamethasone

Dexamethasone is a corticosteroid and an immunomodulator/immunosuppressant that has been used to treat various inflammatory conditions, including but not limited to, rheumatoid arthritis, bronchospasm, lupus, etc. Dexamethasone is an agonist of the glucocorticoid receptor and upon binding activates glucocorticoid signaling leading to the suppression of immune responses. Dexamethasone has been permitted Emergency Use Authorization (EUA) by the FDA for the treatment of severe COVID cases that require hospitalization and supplemental oxygen. The Randomized Evaluation of COVID-19 Therapy (RECOVERY) trial found that Dexamethasone treatment reduced mortality from COVID when compared to those who received standard care. Dexamethasone has also been permitted EUA to be used in conjunction with remdesivir when patients require increasing amounts of oxygen.

Prednisone

Prednisone is a corticosteroid and an immunomodulator/immunosuppressant that has been used to treat various inflammatory conditions, including but not limited to, asthma, chronic obstructive pulmonary disease, rheumatoid arthritis, etc. Prednisone is an agonist of the glucocorticoid receptor and upon binding activates glucocorticoid signaling leading to the suppression of immune responses. Prednisone has been permitted EUA by the FDA for the treatment of severe COVID cases that require hospitalization and supplemental oxygen as an alternative to Dexamethasone.

Methylprednisone

Methylprednisone is a synthetic glucocorticoid primarily used for anti-inflammatory and immunosuppression. Methylprednisone is an agonist of the glucocorticoid receptor and upon binding activates glucocorticoid signaling leading to the suppression of immune responses. Methylprednisone has been permitted EUA by the FDA for the treatment of severe COVID cases that require hospitalization and supplemental oxygen as an alternative to Dexamethasone.

Hydrocortisone

Hydrocortisone is a glucocorticoid and is the medication form of the hormone cortisol. Hydrocortisone is used for the treatment of autoimmune disorders and immune suppression. Hydrocortisone is an agonist of the glucocorticoid receptor and upon binding activates glucocorticoid signaling leading to the suppression of immune responses. Hydrocortisone has been permitted EUA by the FDA for the treatment of severe COVID cases that require hospitalization and supplemental oxygen as an alternative to Dexamethasone. A meta-analysis study published by the World Health Organization entitled Rapid Evidence Appraisal for COVID-19 Therapies (REACT) found that hydrocortisone was effective in reducing mortality rate of critically ill COVID-19 patients when compared to standard care.

Baricitinib (Olumiant)

Baricitinib is an inhibitor of janus kinase (JAK) that is often used in the treatment of rheumatoid arthritis in addition to other autoimmune diseases. Baricitinib has been permitted EUA by the FDA to be used only in combination with remdesivir when, in rare circumstances, corticosteroids can be used. Baricitinib has been shown to specifically inhibit the activity of Janus kinase 1 and 2.

Others

Other immunomodulators include ocilizumab and sarilumab, monoclonal antibodies that target cytokines or their receptors, and other JAK inhibitors (e.g., tofacitinib, upadacitinib and ruxolitinib, etc.).

The present therapy may also be used in conjunction with plasma therapy and/or invermectin.

Methods of Administration

The route of administration may be selected according to a variety of factors including, but not limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound may depend, at least, on the particular method of use, the subject being treated, the severity of the affliction, and the manner of administration of the therapeutic composition. A "therapeutically effective amount" of a composition is a quantity of a specified compound or prodrug sufficient to achieve a desired effect in a subject (e.g., patient) being treated. For example, this may be the amount of a subject compound or prodrug necessary to prevent, inhibit, reduce or relieve a disease or disorder in a subject. Ideally, a therapeutically effective amount of a compound is an amount sufficient to prevent, inhibit, reduce or relieve a disease or disorder in a subject without causing a substantial cytotoxic effect on host cells in the subject.

Therapeutically effective doses of a subject compound or prodrug or pharmaceutical composition can be determined by one of skill in the art, with a goal of achieving local (e.g., tissue) concentrations that are at least as high as the $EC_{50}$ of an applicable compound disclosed herein.

An example of a dosage range is from 0.1 to 200 mg/kg body weight orally in single or divided doses. In some embodiments, a dosage range is from 1.0 to 100 mg/kg body weight orally in single or divided doses, including from 1.0 to 50 mg/kg body weight, from 1.0 to 25 mg/kg body weight, from 1.0 to 10 mg/kg body weight (assuming an average body weight of approximately 70 kg; values may be adjusted accordingly for persons weighing more or less than average). For oral administration, the compositions are, for example, provided in the form of a tablet containing from about 10 to about 1000 mg of the active ingredient, such as 25 to 750 mg, or 50 to 500 mg, for example 75 mg, 100 mg, 200 mg, 250 mg, 400 mg, 500 mg, 600 mg, 750 mg, or 1000 mg of the active ingredient for the symptomatic adjustment of the dosage to the subject being treated. In certain embodiments of an oral dosage regimen, a tablet containing from 500 mg to 1000 mg active ingredient is administered once (e.g., a loading dose) followed by administration of ½ (i.e., half) dosage tablets (e.g., from 250 to 500 mg) each 6 to 24 hours for 3 days or more.

The specific dose level and frequency of dosage for any particular subject may be varied and may depend upon a variety of factors, including the activity of the subject compound or prodrug, the metabolic stability and length of action of that compound, the age, body weight, general health, sex and diet of the subject, mode and time of administration, rate of excretion, drug combination, and severity of the condition of the host undergoing therapy.

Embodiments of the present disclosure also include combinations of one or more disclosed compounds or prodrugs with one or more other agents or therapies useful in the treatment of a disease or disorder. The term "administration in combination with" refers to both concurrent and sequential administration of the active agents.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Following examples illustrate procedures for practicing certain embodiments of the invention. These examples are not limiting.

EXAMPLE 1

Administration of Fostamatinib to COVID-19 Patients

As noted above, COVID-19 infection may lead to downstream events such as cytokine storm, NETosis, and platelet activation culminating in ALI, ARDS, and thrombosis. Fostamatinib is a reversible, oral SYK inhibitor, that has been evaluated in >3500 patients with different diseases. Fostamatinib was approved in 2018 in the US and subsequently in Canada and Europe for the treatment of chronic immune thrombocytopenia (ITP), and two randomized studies showed increased platelet counts and decreased bleeding episodes in ITP patients. Fostamatinib has consistently demonstrated a manageable safety profile across a spectrum of diseases. In rheumatoid arthritis (RA) patients, fostamatinib was shown to reduce plasma levels of IL-6 within the first week of treatment (Weinblatt et al. *Arth Rheum* 2008;58: 3309-18). The active metabolite, R406, was shown to be protective in mice with LPS-induced ALI (Nadeem A et al. *Int Immunopharm* 2019;68:39-47). Separately, SYK inhibition through platelet receptors have been shown to decrease the incidence of thrombosis in mouse models of thromboembolism (Van Eeuwijk J M M et al. *Arterioscler Thromb Vasc Biol.*, 2016;36:1247-53.) Fostamatinib has also been shown to block NETosis in human neutrophils in in vitro studies (Strich J R et al. *J infect Dis.* 2020;jiaa789). Patients with ARDS have increased levels of mucin-1 (MUC1), a major component of mucus in the airways. A high-content imaging screen identified fostamatinib as a drug with potential to reduce MUC1 levels in ARDS, and R406 reduced MUC1 in a mouse model of ALI (Kost-Alimova M et al. *Cell Rep Med.* 2020;1(8):100137). Collectively, these studies provide strong evidence that fostamatinib is a potential therapy for COVID-19 through SYK inhibition.

A clinical study is conducted to test fostamatinib in hospitalized COVID-19 patients.

Figure 3:
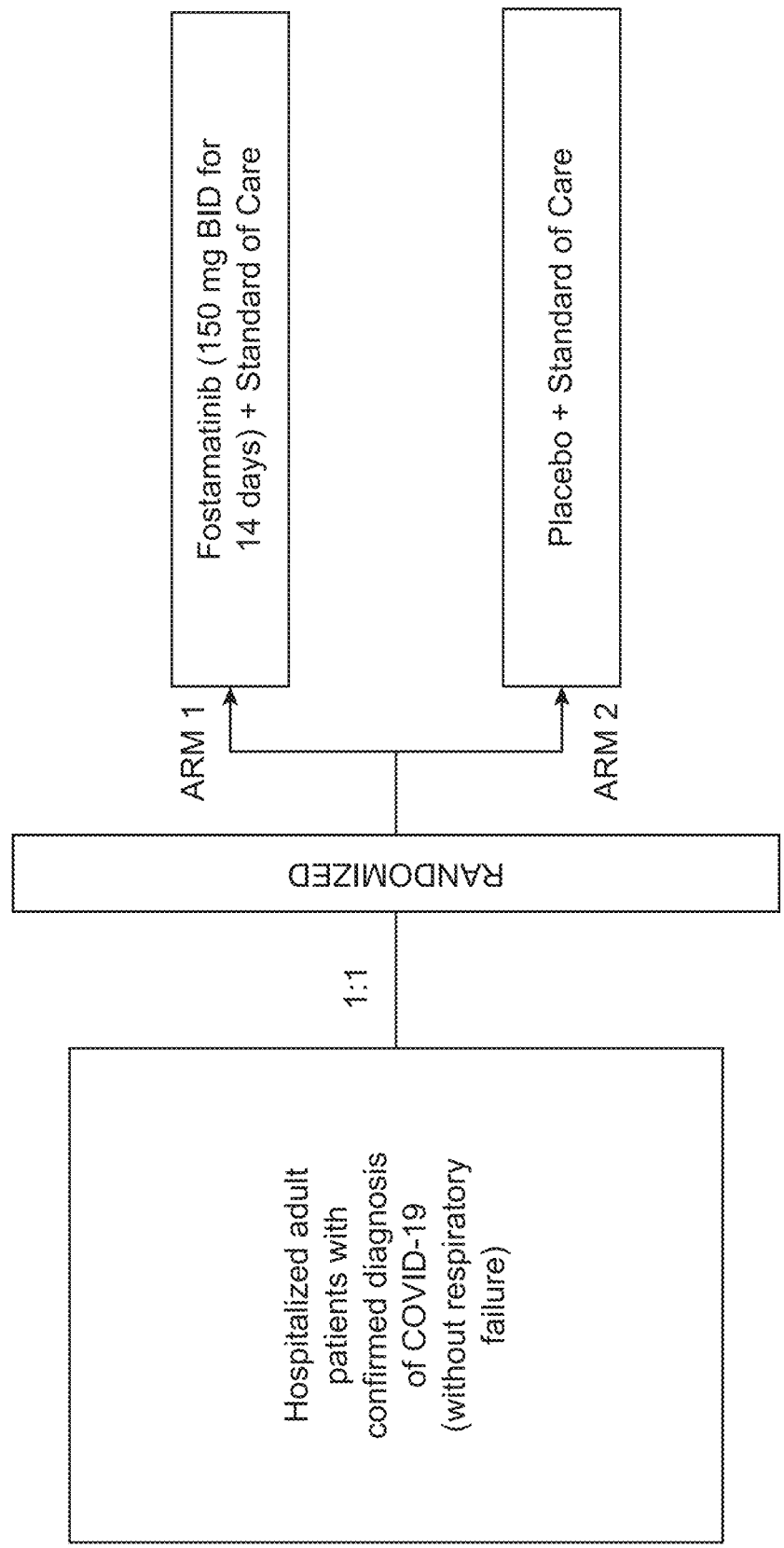
FIG. 3 shows the design for a clinical trial.

The design for this clinical study is provided in FIG. 3. A double-blind, randomized, placebo-controlled, adaptive design, multi-center, Phase 3 study is conducted to evaluate the safety and efficacy of fostamatinib in adult patients with COVID-19.

Inclusion criteria, must satisfy all of the following: age of more than 18 years and less than 100 years; hospitalized COVID-19 subjects without respiratory failure who are either not receiving any oxygen therapy or are receiving supplemental oxygen via mask or nasal prongs; male or non-pregnant, non-lactating female with COVID-19 infection documented by a hospital approved diagnostic test (e.g., a Food and Drug Administration authorized test in the US) within 7 days prior to randomization.

Exclusion criteria, must not have any of the following: pregnant or lactating female of childbearing potential; use of extracorporeal membrane oxygenation (ECMO) or ARDS; uncontrolled hypertension (systolic blood pressure [BP] ≥160 mmHg and/or diastolic BP≥100 mmHg); unstable angina; congestive heart failure of New York Heart Association classification III or IV; serious cardiac arrhythmia requiring treatment; history of myocardial infarction within 3 months prior to screening.

After informed consent, patients are treated twice daily for 14 days with fostamatinib or placebo. Each fostamatinib dose is between 100 to 200 mg, thereby administering between 200 and 400 mg of fostamatinib per day. For example, each fostamatinib dose is 125 mg, 150 mg, 175 mg, or 200 mg. Fostamatinib is administered orally. Other routes of administration are also tested.

Fostamatinib is administered as TAVALISSE™, which contains fostamatinib disodium hexahydrate. TAVALISSE™ oral tablet can contain 100 mg or 150 mg fostamatinib, which is equivalent to 126.2 mg or 189.3 mg fostamatinib disodium hexahydrate, respectively. The inactive ingredients in the tablet core are mannitol, sodium bicarbonate, sodium starch glycolate, povidone, and magnesium stearate. The inactive ingredients in the film coating are polyvinyl alcohol, titanium dioxide, polyethylene glycol 3350, talc, iron oxide yellow, and iron oxide red.

In addition to fostamatinib or placebo, the enrolled participants are provided the standard of care for COVID-19 patients.

The primary outcome measure is the progression to severe/critical disease within 29 days of first dose of study treatment.

Outcomes: Compared to the placebo group, in the fostamatinib group, a significantly smaller percentage of patients is expected to develop severe or critical disease within 29 days of first dose of study treatment. The following outcomes are expected: 1) fostamatinib is expected to significantly reduce the percentage of COVID-19 infected patients that develop severe disease that requires intensive care; 2) within the patients that develop severe disease that requires intensive care, fostamatinib is expected to significantly reduce the percentage of patients that develop ARDS; and 3) within the patients that develop ARDS, fostamatinib is expected to significantly reduce the number of patients that die.

EXAMPLE 2

Treatment of Specific COVID-19 Symptoms Using Fostamatinib

Further outcomes—In COVID-19 infected patients, fostamatinib is expected to significantly reduces certain specific symptoms of COVID-19. Particularly, compared to the placebo group, in the fostamatinib group, the occurrence of several severe symptoms of COVID-19 is expected to be significantly reduced. For example, smaller percentage of patients are expected to develop one or more of the following symptoms: AKI; Kidney malfunction; acute lung injury, etc.; thrombosis; and coagulopathy.

These symptoms are expected to be reduced in the fostamatinib group via one or more of the following mechanisms: inhibition of neutrophil lung infiltration and activation, inhibition of IL-17 production, inhibition of cytokine storm, inhibition of NETosis, inhibition of Fc receptor dependent mast cell degranulation, inhibition of Fc receptor dependent macrophage TNF-α release, inhibition of Fc receptor dependent neutrophil oxidative burst, inhibition of B-cell receptor mediated B cell CD69 upregulation, inhibition of SYK-mediated platelet aggregation, and inhibition of mucin-1 expression in lung epithelia, and inhibition of antibody induced acute kidney injury.

EXAMPLE 3

Studying Fostamatinib Administered in Combination With One or More Other Therapeutic Agents A study is conducted generally as described in Example 1 with additional arms that include a combination of fostamatinib with one or more other therapeutic agents. These other therapeutic agents include those described above under the section header "Combination therapies" above. Typically, one arm in such study comprises administering fostamatinib in combination with an additional therapeutic plus standard of care and other arm comprises administering placebo in combination with the additional therapeutic plus standard of care.

Outcome: Compared to the patients that receive only fostamatinib, the patients that receive fostamatinib in combination with certain other therapeutics are expected to exhibit further significant reduction in the occurrence of specific disease symptoms and/or disease severity.

What is claimed is:

1. A method of treatment of a COVID-19 infection, comprising:
   administering to a patient having or suspected of having the COVID-19 infection, a compound, wherein the compound is of the formula:

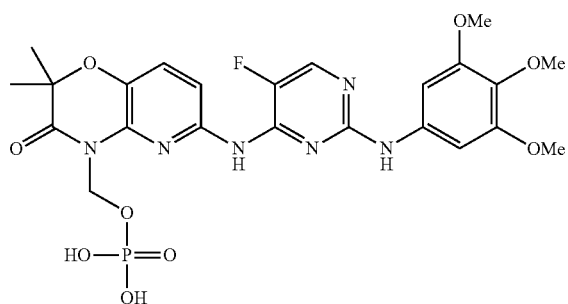 [SMILES: COc1cc(Nc2ncc(F)c(Nc3ccc4c(n3)N(COP(=O)(O)O)C(=O)C(C)(C)O4)n2)cc(OC)c1OC]

or a pharmaceutically acceptable salt thereof, or

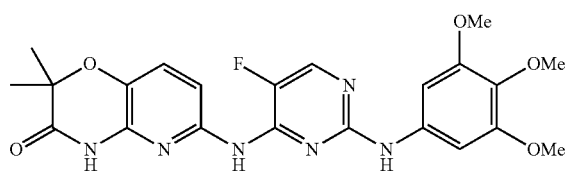 [SMILES: COc1cc(Nc2ncc(F)c(Nc3ccc4c(n3)NC(=O)C(C)(C)O4)n2)cc(OC)c1OC]

or a pharmaceutically acceptable salt thereof.

2. The method of claim 1, wherein the patient has or is expected to develop acute respiratory distress syndrome.

3. The method of claim 1, wherein the patient has a cough but does not have acute respiratory distress syndrome.

4. The method of claim 1, wherein the patient is over the age of 60 and/or has one or more other lung diseases.

5. The method of claim 4, wherein the patient has or has a history of having asthma, pneumothorax, atelectasis, bronchitis, chronic obstructive pulmonary disease, lung cancer or pneumonia.

6. The method of claim 1, wherein the patient has or is expected to develop acute kidney injury.

7. The method of claim 1, wherein the patient has reduced kidney function but does not have acute kidney injury.

8. The method of claim 1, wherein the patient is over the age of 60 and/or has one or more other kidney diseases.

9. The method of claim 1, wherein the patient has or has a history of having dialysis treatments and/or has had a kidney transplant.

10. The method of claim 1, wherein the patient has or is expected to develop thrombosis.

11. The method of claim 1, wherein the patient has a prothrombotic coagulation profile but does not have thrombosis.

12. The method of claim 11, wherein the patient has increased levels of D-dimer.

13. The method of claim 1, wherein the patient is over the age of 60 and/or has one or more risk factors for developing thrombosis.

14. The method of claim 1, wherein the patient has or has had a thrombotic event.

15. The method of claim 1, wherein the administering is systemically administering.

16. The method of claim 15, wherein the administering is done orally or intravenously.

17. The method of claim 1, wherein the administering is done by pulmonary administration.

18. The method of claim 17, wherein the administering is done using an inhaler or nebulizer.

19. The method of claim 1, wherein the patient is in intensive care.

20. The method of claim 1, wherein the compound is of the formula:

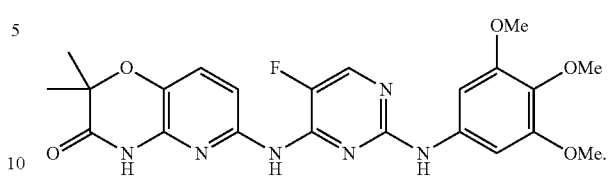

21. A method for treating acute respiratory distress syndrome, comprising:
administering to a patient having, suspected of having or expected to develop acute respiratory distress syndrome, a compound, wherein the compound is of the formula:

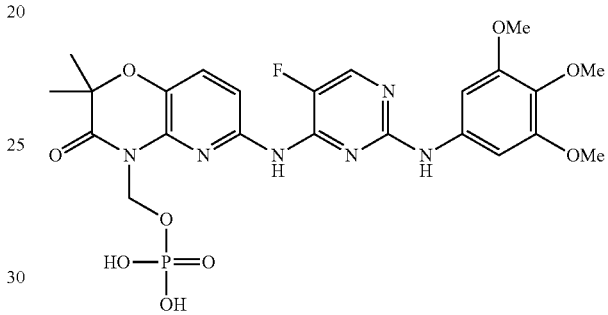

or a pharmaceutically acceptable salt thereof, or

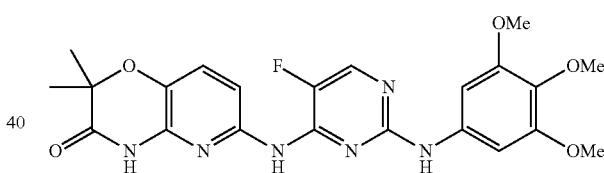

or a pharmaceutically acceptable salt thereof.

22. The method of claim 21, wherein the patient has a COVID-19 infection.

23. The method of claim 21, wherein the patient has or is expected to develop acute respiratory distress syndrome.

24. The method of claim 21, wherein the patient has a cough but does not have acute respiratory distress syndrome.

25. The method of claim 21, wherein the patient is over the age of 60 and/or has one or more other lung diseases.

26. The method of claim 25, wherein the patient has or has a history of having asthma, pneumothorax, atelectasis, bronchitis, chronic obstructive pulmonary disease, lung cancer or pneumonia.

27. The method of claim 21, wherein the administering is systemically administering.

28. The method of claim 27, wherein the administering is done orally or intravenously.

29. The method of claim 21, wherein the administering is done by pulmonary administration.

30. The method of claim 29, wherein the administering is done using an inhaler or nebulizer.

31. The method of claim 21, wherein the patient is in intensive care.

32. The method of claim 21, wherein the compound is of the formula:

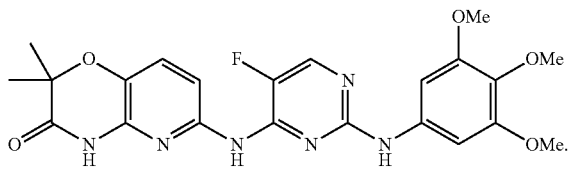 [SMILES: COc1cc(Nc2ncc(F)c(Nc3ccc4c(n3)NC(=O)C(C)(C)O4)n2)cc(OC)c1OC]

33. The method of claim 1, wherein the compound is of the formula:

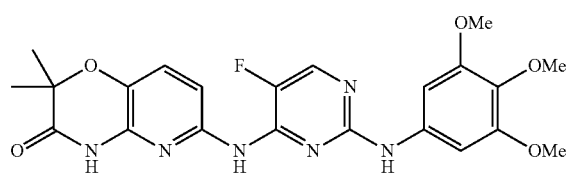 [SMILES: COc1cc(Nc2ncc(F)c(Nc3ccc4c(n3)NC(=O)C(C)(C)O4)n2)cc(OC)c1OC]

or a pharmaceutically acceptable salt thereof.

34. The method of claim 21, wherein the compound is of the formula:

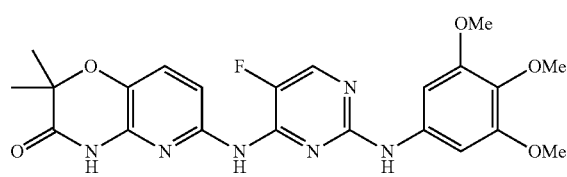 [SMILES: COc1cc(Nc2ncc(F)c(Nc3ccc4c(n3)NC(=O)C(C)(C)O4)n2)cc(OC)c1OC]

or a pharmaceutically acceptable salt thereof.

35. The method of claim 1, wherein the compound is of the formula:

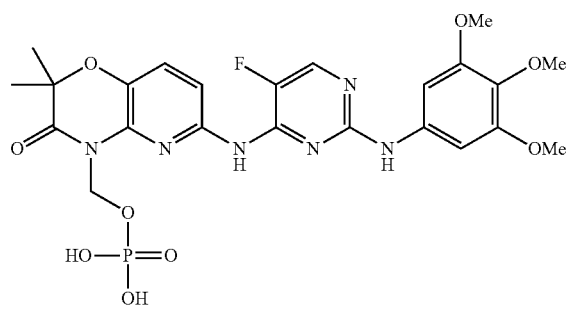 [SMILES: COc1cc(Nc2ncc(F)c(Nc3ccc4c(n3)N(COP(=O)(O)O)C(=O)C(C)(C)O4)n2)cc(OC)c1OC]

or a pharmaceutically acceptable salt thereof.

36. The method of claim 21, wherein the compound is of the formula:

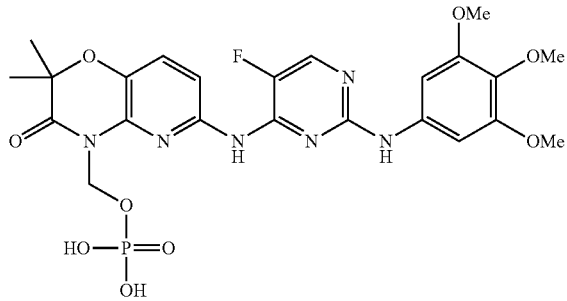 [SMILES: COc1cc(Nc2ncc(F)c(Nc3ccc4c(n3)N(COP(=O)(O)O)C(=O)C(C)(C)O4)n2)cc(OC)c1OC]

or a pharmaceutically acceptable salt thereof.

37. A method for treating sepsis, comprising:
administering to a patient having, suspected of having or expected to develop sepsis, a compound, wherein the compound is of the formula:

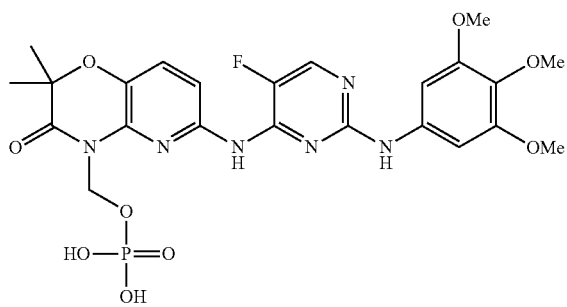 [SMILES: COc1cc(Nc2ncc(F)c(Nc3ccc4c(n3)N(COP(=O)(O)O)C(=O)C(C)(C)O4)n2)cc(OC)c1OC]

or a pharmaceutically acceptable salt thereof, or or a pharmaceutically acceptable salt thereof.

38. The method of claim 37, wherein the patient has a COVID-19 infection.

39. The method of claim 37, wherein the patient has acute respiratory distress syndrome.

* * * * *